US008084020B2

(12) United States Patent
Exley et al.

(10) Patent No.: US 8,084,020 B2

(45) Date of Patent: Dec. 27, 2011

(54) USE OF ANTI-CD1 ANTIBODIES FOR THE MODULATION OF IMMUNE RESPONSES

(75) Inventors: Mark A. Exley, Chestnut Hill, MA (US); Steven P. Balk, Needham, MA (US); Simon C. Yue, Brighton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 995 days.

(21) Appl. No.: 10/513,109

(22) PCT Filed: May 1, 2003

(86) PCT No.: PCT/US03/13741

§ 371 (c)(1), (2), (4) Date: Jun. 30, 2005

(87) PCT Pub. No.: WO03/092615

PCT Pub. Date: Nov. 13, 2003

(65) Prior Publication Data

US 2006/0002927 A1 Jan. 5, 2006

Related U.S. Application Data

(60) Provisional application No. 60/376,713, filed on May 1, 2002.

(51) Int. Cl.

| | |
|---|---|
| ***A61K 45/00*** | (2006.01) |
| ***A61K 39/395*** | (2006.01) |
| ***A61K 39/00*** | (2006.01) |
| *C07K 14/00* | (2006.01) |
| *C07K 16/00* | (2006.01) |
| *C07K 16/28* | (2006.01) |

(52) U.S. Cl. ................... 424/85.1; 424/85.2; 424/130.1; 424/133.1; 424/141.1; 424/143.1; 424/152.1; 424/156.1

(58) Field of Classification Search ........................ None
See application file for complete search history.

(56) References Cited

U.S. PATENT DOCUMENTS

| | | | | |
|---|---|---|---|---|
| 5,679,347 | A * | 10/1997 | Porcelli et al. | 424/184.1 |
| 5,853,737 | A * | 12/1998 | Modlin et al. | |
| 6,238,676 | B1 * | 5/2001 | Porcelli et al. | |
| 2001/0051156 | A1 | 12/2001 | Zeng et al. | |
| 2002/0094542 | A1 * | 7/2002 | Leskovar | 435/7.1 |
| 2002/0115624 | A1 * | 8/2002 | Behar et al. | 514/42 |
| 2006/0002927 | A1 * | 1/2006 | Exley et al. | 424/144.1 |

FOREIGN PATENT DOCUMENTS

| | | | |
|---|---|---|---|
| EP | 0 677 533 | A2 * | 10/1995 |
| EP | 1 025 854 | A1 * | 8/2000 |
| WO | WO 96/33730 | * | 10/1996 |
| WO | WO 99/34209 | * | 7/1999 |
| WO | WO 01/98357 | A2 * | 12/2001 |

OTHER PUBLICATIONS

Amano et al (J. Immunol. 1998, 161: 1710-1717).*
Landes Bioscience: APC Dysfunction in SLE, http://www.ncbi.nlm.nih.gov/books/bv.fcgi?rid=eurekah.section.13810, 2008.*
Zeng et al (J. Clin. Invest. Oct. 2003, 112(8): 1211-1222).*
Rhee et al (FASEB J. Mar. 20, 2002, vol. 16, No. 5, pp. A1228).*
Rhee et al (J. Surg. Res. 2003, 115(1): 74-81).*
Fahey et al., Clinical Experimental Immunology, 1992, 88: 1-5.*
Letvin, Science, 1998, 280: 1875-1880.*
Machuca et al. Intervirology 1999, 42: 37-42.*
Parker and Watkins (Brit. J. Surgery. 2001, 88: 22-30).*
Schinkel (J. Interferon & Cytokine Research, 2003, 23: 341-349).*
De St. Groth et al (Immunology and Cell Biology 2004, 82: 260-268).*
Teng et al (Journal of Immunology, 2009, 182: 3366-3371).*
Mocellin et al (J. Leuk. Biol. 2005, 78: 1043-1051).*
Balk et al., "Isolation and Characterization of a cDNA and Gene Coding for a Fourth CD1 Molecule," *Proc. Natl. Acad. Sci. U.S.A.* 86:252-256 (1989).*
Bendelac et al., "Mouse CD1-Specific NK1 T Cells: Development, Specificity, and Function," *Annu. Rev. Immunol.* 15:535-562 (1997).*
Bender et al., "T Cell Receptor Repertoire in Polymyositis: Clonal Expansion of Autoaggressive $CD8^+$ T Cells," *J. Exp. Med.* 181:1863-1868 (1995).*
Benlagha et al., "In Vivo Identification of Glycolipid Antigen-Specific T Cells Using Fluorescent CD1d Tetramers," *J. Exp. Med.* 191:1895-1903 (2000).*
Bleicher et al., "Expression of Murine CD1 on Gastrointestinal Epithelium," *Science* 250:679-682 (1990).*
U.S. Appl. No. 09/885,768, filed Jun. 19, 2001, Exley et al.*
Blumberg et al., "Human Intestinal Intraepithelial Lymphocytes are Derived from a Limited Number of T Cell Clones that Utilize Multiple Vβ T Cell Receptor Genes," *J. Immunol.* 150:5144-5153 (1993).
Bubley and Balk, "Treatment of Metastatic Prostate Cancer. Lessons from the Androgen Receptor," *Hematol. Oncol. Clin. North Am.* 10:713-725 (1996).

(Continued)

*Primary Examiner* — Gerald R Ewoldt
*Assistant Examiner* — Marianne DiBrino
(74) *Attorney, Agent, or Firm* — Clark & Elbing LLP; Kristina Bieker-Brady

(57) ABSTRACT

The invention provides methods for the administration of an anti-CD 1 antibody for the treatment or prevention of a variety of disorders, such as autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer.

6 Claims, 31 Drawing Sheets

OTHER PUBLICATIONS

Carnaud et al., "Cross-Talk Between Cells of the Innate Immune System: NKT Cells Rapidly Activate NK Cells," *J. Immunol.* 163:4647-4650 (1999).
Catalona, "Management of Cancer of the Prostate," *N. Engl. J. Med.* 331:996-1004 (1994).
Cho et al., "A Genome-Wide Transcriptional Analysis of the Mitotic Cell Cycle," *Mol. Cell* 2:65-73 (1998).
Chott et al., "A Common TCR β-Chain Expressed by $CD8^+$ Intestinal Mucosa T Cells in Ulcerative Colitis," *J. Immunol.* 156:3024-3035 (1996).
Colgan et al., "Ligation of Intestinal Epithelial CD1d Induces Bioactive IL-10: Critical Role of the Cytoplasmic Tail in Autocrine Signaling," *Proc. Natl. Acad. Sci. U.S.A.* 96: 13938-13943 (1999).
Cui et al., "Requirement for Vα 14 NKT Cells in IL-12-Mediated Rejection of Tumors," *Science* 278:1623-1626 (1997).
Dellabona et al., "An Invariant Vα24-JαQ/Vβ11 T Cell Receptor is Expressed in All Individuals by Clonally Expanded $CD4^-8^-$ T Cells," *J. Exp. Med.* 180:1171-1176 (1994).
Dezutter-Dambuyant et al., "Cleavage of Langerhans Cell Surface CD1a Molecule by Trypsin," *Res. Immunol.* 140:377-390 (1989).
Exley et al., "Association of Phosphatidylinositol 3-Kinase with a Specific Sequence of the T Cell Receptor ζ Chain is Dependent on T Cell Activation," *J. Biol. Chem.* 269:15140-15146 (1994).
Exley et al., "Requirements for CD1d Recognition by Human Invariant $V\alpha24^+$ $CD4^-$ $CD8^-$ T Cells," *J. Exp. Med.* 186:109-120 (1997).
Exley et al., "CD161 (NKR-P1A) Costimulation of CD1d-Dependent Activation of Human T Cells Expressing Invariant Vα24JαQ T Cell Receptor α Chains," *J. Exp. Med.* 188:867-876 (1998).
Exley et al., "CD1d Structure and Regulation on Human Thymocytes, Peripheral Blood T Cells, B Cells and Monocytes," *Immunology* 100:37-47 (2000).
Exley et al., "A Major Fraction of Human Bone Marrow Lymphocytes are Th2-Like CD1d-Reactive T Cells that can Suppress Mixed Lymphocyte Responses," *J. Immunol.* 167:5531-5534 (2001).
Exley et al., "CD1d-Reactive T-Cell Activation Leads to Amelioration of Disease Caused by Diabetogenic Encephalomyocarditis Virus," *J. Leukoc. Biol.* 69:713-718 (2001).
Falcone et al., "A Defect in Interleukin 12-Induced Activation and Interferon γ Secretion of Peripheral Natural Killer T Cells in Nonobese Diabetic Mice Suggests New Pathogenic Mechanisms for Insulin-Dependent Diabetes Mellitus," *J. Exp. Med.* 190:963-972 (1999).
Farace et al., "T Cell Repertoire in Patients with B Chronic Lymphocytic Leukemia," *J. Immunol.* 153:4281-4290 (1994).
Fitzgerald et al., "Analysis of Clonal $CD8^+$ T Cell Expansions in Normal Individuals and Patients with Rheumatoid Arthritis," *J. Immunol.* 154:3538-3547 (1995).
Gavilondo et al., "Antibody Engineering at the Millennium," *Biotechniques* 29:128-145 (2000).
Giron et al., "Inhibition of Virus-Induced Diabetes Mellitus by Interferon is Influenced by the Host Strain," *Proc. Soc. Exp. Biol. Med.* 173:328-331 (1983).
Gorochov et al., "Oligoclonal Expansion of $CD8^+$ $CD57^+$ T Cells with Restricted T-Cell Receptor β Chain Variability After Bone Marrow Transplantation," *Blood* 83:587-595 (1994).
Grunewald et al., "$CD^+$ and $CD8^+$ T Cell Expansions Using Selected TCR V and J Gene Segments at the Onset of Giant Cell Arteritis," *Arthritis Rheum.* 37:1221-1227 (1994).
Hammerberg et al., "Reversal of Immunosuppression Inducible Through Ultraviolet-Exposed Skin by In Vivo Anti-CD11b Treatment," *J. Immunol.* 157:5254-5261 (1996).
Hingorani et al., "Oligoclonality of Vβ3 TCR Chains in the $CD8^+$ T Cell Population of Rheumatoid Arthritis Patients," *J. Immunol.* 156:852-858 (1996).
Hong and Van Kaer, "Immune Privilege: Keeping an Eye on Natural Killer T Cells," *J. Exp. Med.* 190:1197-1200 (1999).
Huber et al., "$V\gamma4^+$ T Cells Promote Autoimmune $CD8^+$ Cytolytic T-Lymphocyte Activation in Coxsackievirus B3-Induced Myocarditis in Mice: Role for $CD4^+$ Th1 Cells," *J. Virol.* 76:10785-10790 (2002).
Illés et al., "Differential Expression of NK T Cell Vα24JαQ Invariant TCR Chain in the Lesions of Multiple Sclerosis and Chronic Inflammatory Demyelinating Polyneuropathy," *J. Immunol.* 164:4375-4381 (2000).
Ito et al., "Involvement of Decidual Vα14 NKT Cells in Abortion," *Proc. Natl. Acad. Sci. U.S.A.* 97:740-744 (2000).
Jameson et al., "The T Cell Receptor Vα11 Gene Family. Analysis of Allelic Sequence Polymorphism and Demonstration of Jα Region-Dependent Recognition by Allele-Specific Antibodies," *J. Immunol.* 147:3185-3193 (1991).
Johnson and Wu, "Kabat Database and its Applications: Future Directions," *Nucleic Acids Res.* 29:205-206 (2001).
Kahn-Perles et al., "Delineation of Three Subsets of Class I Human T Antigens (HTA) on Molt-4 Cells: Serologic and Regulatory Relationship to HLA Class I Antigens," *J. Immunol.* 134:1759-1765 (1985).
Karnbach et al., "Immune Rejection of a Large Sarcoma Following Cyclophosphamide and IL-12 Treatment Requires Both NK and NK T Cells and is Associated with the Induction of a Novel NK T Cell Population," *J. lmmunol.* 167:2569-2576 (2001).
Kasinrerk et al., "CD1 Molecule Expression on Human Monocytes Induced by Granulocyte-Macrophage Colony-Stimulating Factor," *J. Immunol.* 150:579-584 (1993).
Kawano et al., "Antitumor Cytotoxicity Mediated by Ligand-Activated Human Vα24 NKT Cells," *Cancer Res.* 59:5102-5105 (1999).
Kent et al., "Noncanonical Vα24JαQ T Cells with Conservative α Chain CDR3 Region Amino Acid Substitutions are Restricted by CD1d," *Hum. Immunol.* 60:1080-1089 (1999).
Kuwana et al., "Highly Restricted TCR-αβ Usage by Autoreactive Human T Cell Clones Specific for DNA Topoisomerase I," *J. Immunol.* 158:485-491 (1997).
Lehmann et al., "IL-12p40-Dependent Agonistic Effects on the Development of Protective Innate and Adaptive Immunity Against *Salmonella enteritidis*," *J. lmmunol.* 167:5304-5315 (2001).
Lockhart et al., "Expression Monitoring by Hybridization to High-Density Oligonucleotide Arrays," *Nat. Biotechnol.* 14:1675-1680 (1996).
Maldonado-López et al., "$CD8\alpha^+$ and $CD8\alpha^-$ Subclasses of Dendritic Cells Direct the Development of Distinct T Helper Cells In Vivo," *J. Exp. Med.* 189:587-592 (1999).
Martin et al., "Structure and Expression of the Human Thymocyte Antigens CD1a, CD1b, and CD1c," *Proc. Natl. Acad. Sci. U.S.A.* 84:9189-9193 (1987).
Matsuda et al., "Tracking the Response of Natural Killer T Cells to a Glycolipid Antigen Using CD1d Tetramers," *J. Exp. Med.* 192:741-753 (2000).
Milner et al., "Differential Responses of Invariant Vα24JαQ T Cells and MHC Class II-Restricted $CD4^+$ T Cells to Dexamethasone," *J. Immunol.* 163:2522-2529 (1999).
Monson et al., "Differential Expression of NKT Cells in Multiple Sclerosis Patients," *J. Neuroimmunol.* 118:87 (2001).
Moss et al., "Clonal Populations of $CD4^+$ and $CD8^+$ T Cells in Patients with Multiple Myeloma and Paraproteinemia," *Blood* 87:3297-3306 (1996).
Naidenko et al., "Binding and Antigen Presentation of Ceramide-Containing Glycolipids by Soluble Mouse and Human CD1d Molecules," *J. Exp. Med.* 190:1069-1079 (1999).
Nicol et al., "Human Invariant $V\alpha24^+$ Natural Killer T Cells Activated by α-Galactosylceramide (KRN7000) have Cytotoxic Anti-Tumour Activity Through Mechanisms Distinct from T Cells and Natural Killer Cells," *Immunology* 99:229-234 (2000).
O'Doherty et al., "Dendritic Cells Freshly Isolated from Human Blood Express CD4 and Mature into Typical Immunostimulatory Dendritic Cells after Culture in Monocyte-Conditioned Medium," *J. Exp. Med.* 178:1067-1078 (1993).
Porcelli et al., "Recognition of Cluster of Differentiation 1 Antigens by Human $CD4^-$ $CD8^-$ Cytolytic T Lymphocytes," *Nature* 341:447-450 (1989).
Porcelli et al., "Analysis of T Cell Antigen Receptor (TCR) Expression by Human Peripheral Blood $CD4^-8^-$ α/β T Cells Demonstrates Preferential Use of Several Vβ Genes and an Invariant TCR α Chain," *J. Exp. Med.* 178:1-16 (1993).

Porcelli and Modlin, "The CD1 System: Antigen-Presenting Molecules for T Cell Recognition of Lipids and Glycolipids," *Annu. Rev. Immunol.* 17:297-329 (1999).
Probert et al., "Persistent Clonal Expansions of Peripheral Blood $CD4^+$ Lymphocytes in Chronic Inflammatory Bowel Disease," *J. Immunol.* 157:3183-3191 (1996).
Prussin and Foster, "TCR Vα24 and Vβ11 Coexpression Defines a Human NK1 T Cell Analog Containing a Unique Th0 Subpopulation," *J. Immunol.* 159:5862-5870 (1997).
Reid et al., "The Control of T Cell Responses by Dendritic Cell Subsets," *Curr. Opin. Immunol.* 12:114-121 (2000).
Reinherz et al., "The Crystal Structure of a T Cell Receptor in Complex with Peptide and MHC Class II," *Science* 286:1913-1921 (1999).
Rissoan et al., "Reciprocal Control of T Helper Cell and Dendritic Cell Differentiation," *Science* 283:1183-1186 (1999).
Shigematsu and Masuda, "Usage of T Cell Receptor (TCR) V β Gene in Ulcerative Colitis," *J. Clin. Lab. Immunol.* 48:177-186 (1996).
Smiley et al., "Immunoglobulin E Production in the Absence of Interleukin-4-Secreting CD1-Dependent Cells," *Science* 275:977-979 (1997).
Sonoda et al., "CD1-Reactive Natural Killer T Cells are Required for Development of Systemic Tolerance Through an Immune-Privileged Site," *J. Exp. Med.* 190:1215-1225 (1999).
Sottini et al., "Selection of T Lymphocytes in Two Rheumatoid Arthritis Patients Defines Different T-Cell Receptor Vβ Repertoires in $CD4^+$ and $CD8^+$ T-Cell Subsets," *J. Autoimmun.* 6:621-637 (1993).
Streilein et al., "Immune Deviation in Relation to Ocular Immune Privilege," *J. Immunol.* 158:3557-3560 (1997).
Streilein et al., "Immune Privilege, T-Cell Tolerance, and Tissue-Restricted Autoimmunity," *Hum. Immunol.* 52:138-143 (1997).
Szalay et al., "Anti-CD1 Monoclonal Antibody Treatment Reverses the Production Patterns of TGF-β2 and Th1 Cytokines and Ameliorates Listeriosis in Mice," *J. Immunol.* 162:6955-6958 (1999).
Tamayo et al., "Interpreting Patterns of Gene Expression with Self-Organizing Maps: Methods and Application to Hematopoietic Differentiation," *Proc. Natl. Acad. Sci. U.S.A.* 96:2907-2912 (1999).
Uyemura et al., "$CD4^+$ Type 1 and $CD8^+$ Type 2 T Cell Subsets in Human Leishmaniasis Have Distinct T Cell Receptor Repertoires," *J. Immunol.* 151:7095-7104 (1993).
van der Vliet et al., "Effects of α-Galactosylceramide (KRN7000), Interleukin-12 and Interleukin-7 on Phenotype and Cytokine Profile of Human $V\alpha24^+$ $V\beta11^+$ T Cells," *Immunology* 98:557-563 (1999).
van der Vliet et al., "Circulating $V\alpha24^+$ $V\beta11^+$ NKT Cell Numbers are Decreased in a Wide Variety of Diseases that are Characterized by Autoreactive Tissue Damage," *Clin. Immunol.* 100:144-148 (2001).
van der Vliet et al., "Potent Expansion of Human Natural Killer T Cells Using α-Galactosylceramide (KRN7000)-Loaded Monocyte-Derived Dendritic Cells, Cultured in the Presence of IL-7 and IL-15," *J. Immunol. Methods* 247:61-72 (2001).
Lyer et al., "The Transcriptional Program in the Response of Human Fibroblasts to Serum," *Science* 283:83-87 (1999).
Wilson et al., "Correction: Extreme Th1 Bias of Invariant Vα24JαQ T Cells in Type 1 Diabetes," *Nature* 399:84 (1999).
Wilson et al., "Multiple Differences in Gene Expression in Regulatory Vα24JαQ T Cells from Identical Twins Discordant for Type 1 Diabetes," *Proc. Natl. Acad. Sci. U.S.A.* 97:7411-7416 (2000).
Wilson et al., "Development of Monoclonal Antibodies to Vα24JαQ T Cells Detects Alterations in Cell Frequency in New-Onset Type 1 Diabetes Patients," *Am. Diabetes Assoc., $61^{st}$ Sci. Sessions* (2001).
Wucherpfennig et al., "T Cell Receptor Vα-Vβ Repertoire and Cytokine Gene Expression in Active Multiple Sclerosis Lesions," *J. Exp. Med.* 175:993-1002 (1992).
Yang et al., "CD1d on Myeloid Dendritic Cells Stimulates Cytokine Secretion from and Cytolytic Activity of Vα24JαQ T Cells: A Feedback Mechanism for Immune Regulation," *J. Immunol.* 165:3756-3762 (2000).
Zeng et al., "A Role for CD1 in the Pathogenesis of Lupus in NZB/NZW Mice," *J. Immunol.* 164:5000-5004 (2000).
Atkins et al., "Phase I evaluation of intravenous recombinant human interleukin 12 in patients with advanced malignancies," *Clin Cancer Res.* 3:409-17, 1997.
Brossay et al., "CD1d-mediated recognition of an α-galactosylceramide by natural killer T cells is highly conserved through mammalian evolution," *J Exp Med.* 188:1521-8, 1998.
Brunda et al., "Antitumor and antimetastatic activity of interleukin 12 against murine tumors," *J Exp Med.* 178:1223-30, 1993.
Gollob et al., "Phase I trial of twice-weekly intravenous interleukin 12 in patients with metastatic renal cell cancer or malignant melanoma: ability to maintain IFN-γ induction is associated with clinical response," *Clin Cancer Res.* 6:1678-92, 2000.

* cited by examiner

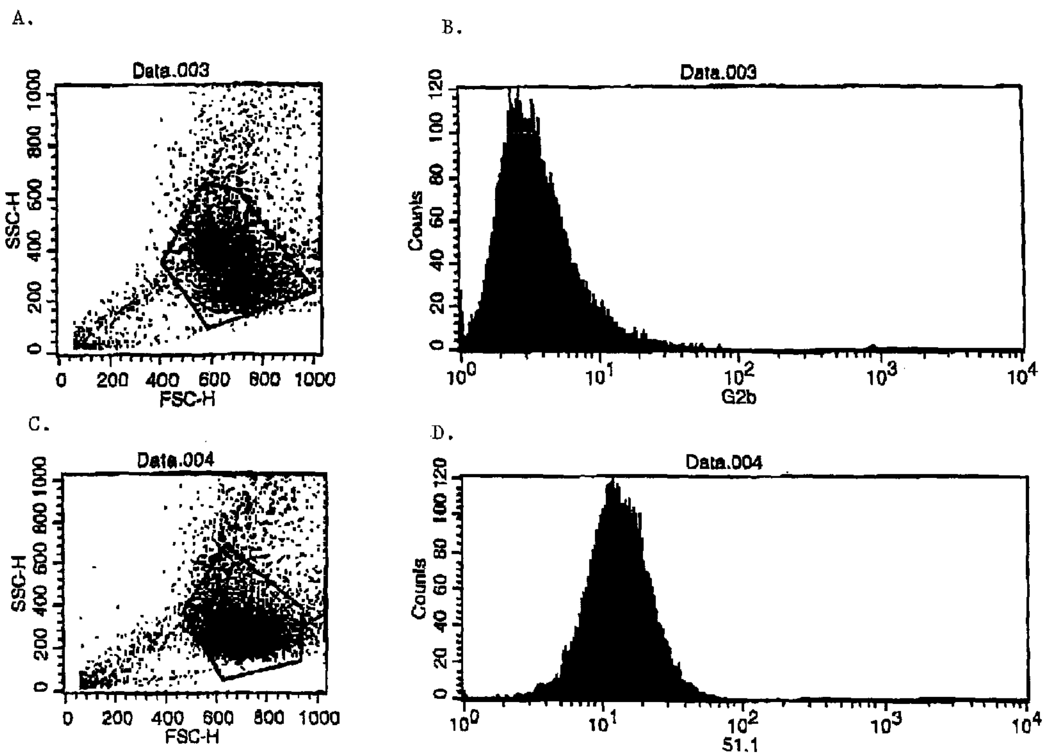
Histogram Statistics
Sample ID: 10th THP-1
Acquisition Date: 08-Feb-02
Gate: G1
Gated Events: 13768
Total Events: 17720
| Events | % Gated | % Total | Mean | Geo Mean | Median |
|---|---|---|---|---|---|
| 13768 | 100.00 | 77.70 | 4.13 | 3.39 | 3.13 |
Histogram Statistics
Sample ID: 10th THP-1
Acquisition Date: 08-Feb-02
Gate: G2
Gated Events: 13165
Total Events: 17506
| Events | % Gated | % Total | Mean | Geo Mean | Median |
|---|---|---|---|---|---|
| 13165 | 100.00 | 75.20 | 14.01 | 12.60 | 12.52 |
Fig. 26A~26D Histogram Statistics Sample ID: C1R mock
Acquisition Date: 06-Feb-02
Gate: G1
Gated Events: 9119
Total Events: 14680

| Events | % Gated | % Total | Mean | Geo Mean | Median |
|---|---|---|---|---|---|
| 9119 | 100.00 | 62.12 | 8.27 | 4.85 | 3.75 |

Histogram Statistics

Sample ID: C1R mock
Acquisition Date: 06-Feb-02
Gate: G2
Gated Events: 10719
Total Events: 17529

| Events | % Gated | % Total | Mean | Geo Mean | Median |
|---|---|---|---|---|---|
| 10719 | 100.00 | 61.15 | 17.40 | 6.59 | 5.83 |

Histogram Statistics

Sample ID: C1Rd
Gate: G1
Total Events: 31666
Acquisition Date: 08-Feb-02
Gated Events: 20086

| Events | % Gated | % Total | Mean | Geo Mean | Median |
|---|---|---|---|---|---|
| 20086 | 100.00 | 63.44 | 6.04 | 4.18 | 4.45 |

Histogram Statistics

Sample ID: C1Rd
Gate: G2
Total Events: 31340
Acquisition Date: 08-Feb-02
Gated Events: 20781

| Events | % Gated | % Total | Mean | Geo Mean | Median |
|---|---|---|---|---|---|
| 20781 | 100.00 | 66.31 | 261.80 | 140.02 | 257.13 |

USE OF ANTI-CD1 ANTIBODIES FOR THE MODULATION OF IMMUNE RESPONSES

CROSS REFERENCE TO THE RELATED APPLICATIONS

This application is a U.S. National Stage application under §371 of PCT/US03/13741, filed May 1, 2003, which claims benefit from U.S. Provisional Application No. 60/376,713, filed May 1, 2002, each of which is hereby incorporated by reference.

STATEMENT AS TO FEDERALLY SPONSORED RESEARCH

This invention was funded by grants AI42955 and CA89567 from the National Institute of Health. The government may have certain rights in the invention.

BACKGROUND OF THE INVENTION

Modulation of the immune system is desirable to treat a variety of diseases and disorders including, but not limited to, autoimmune diseases, infections, allergies, asthma, inflammatory conditions, spontaneous abortion, pregnancy, graft versus host disease, and cancers.

Antigen presenting cells ("APC;" e.g., CD1-expressing monocytes, macrophages, dendritic cells, and B cells) are required for protection against numerous diseases. APCs modulate immune responses by producing antibodies, cytokines, and growth factors; destroying infected and cancerous cells, and activating T cells.

T cells are lymphocytes that participate in multiple cell-mediated immune reactions, such as the recognition and destruction of infected or cancerous cells. Subsets of T cells, such as suppressor, cytotoxic, and helper T cells, mediate different immunologic functions. Suppressor T cells are responsible for turning the immune response off after an infection is cleared. Cytotoxic or "natural killer" T cells destroy infected or cancerous cells. Helper T cells produce cytokines that modulate the activity of cytotoxic T cells and/or antibody-producing B cells.

A subset of helper T cells, Th1 cells, secrete interleukin-1 (IL-1), IL-2, gamma interferon (INF-γ), and IL-2 which enhance cell-mediated responses such as cytotoxic T cell activity and inhibit both Th2 helper T cell activity and humoral immunity mediated by soluble antibodies. Due to their ability to kill antigen-presenting cells and their cytokine-mediated effector activity, Th1 cells are associated with vigorous delayed-type hypersensitivity reactions. Th2 cells, the other subset of helper T cells, are thought to inhibit cell-mediated responses and to enhance the humoral response. Th2 cells secrete IL-4, IL-5, IL-6, IL-9, IL-10, and IL-13 which activate B cell development and antibody production. T cells may also participate in immune deviation responses, such as the suppression of an ongoing immune response which may involve the secretion of TGF-β or IL-10 cytokines (Sonoda et al, J. Ex. Med. 190:1215-1255, 1999; Streilein et al., Hum. Immunol. 52:138-143, 1997; Hong et al, J. Ex. Med. 190, 1197-1200, 1999; Streilein et al., J. Immunol. 158:3557-3560, 1997).

To recognize a particular antigen bound to an antigen-presenting cell, most T cells express a highly specific T cell receptor (TCR) on their cell surface. The chains of the most common T cell receptors are called α and β. A second T cell receptor, found on a minor subpopulation of T cells, is composed of γ and δ chains. The genes for the α, β, γ, and δ chains of the T cell receptors have organizations similar to that of antibody genes: there are libraries of V, D, and J regions from which members are joined to form entire genes.

In contrast to most T cell subpopulations, which have diverse sequences for their TCR-a chain, invariant T cells have a highly conserved invariant TCR-α chain, Vα24-JαQ in humans and Vα14-Jα281 in mice, that pairs preferentially with human Vβ11 or murine Vβ8. These cells are either $CD4^+CD8^-$ or $CD4^-CD8^-$. This invariant TCR is presumed to enable invariant T cells to recognize endogenous or pathogen-derived lipid antigens presented by nonpolymorphic MHC class I-like proteins, called CD1 family members. Humans have four CD1 proteins (CD1a, CD1b, CD1c, and CD1d), but mice have only a duplicated CD1d gene that is highly homologous to human CD1d. Human CD1d is expressed at high levels by thymocytes, at lower levels by B cells and monocytes, and by some cells outside of the lymphoid and myeloid lineages.

Many invariant T cells are distinguished by expression of several cell surface proteins otherwise found largely on natural killer (NK) cells, including CD161 (NKR-P1A) in humans, and a cell surface C-type lectin, NKR-P1C (NK1), in mice. This T cell subpopulation, referred to here as "invariant NK T cells," represents a major fraction of the mature T cells in thymus, the major T cell subpopulation in murine liver, and up to 5% of splenic T cells in some mouse strains.

Murine and human invariant T cells also produce large amounts of the immunoregulatory cytokines IL-4 (a Th2 effector) and IFN-γ (a Th1 effector) in vivo in response to an anti-CD3 antibody or to CD1d. These cytokines allow the cells to participate in both Th2 and Th1 responses. The role of invariant T cells in augmenting the Th2 response, which appears to be protective in some autoimmune diseases, is further supported by the presence of defects in invariant T cells in a number of human and murine models of autoimmune diseases, including type 1 diabetes. Thus, alterations in the balance between Th1 and Th2 responses induced by invariant T cells may play a role in the development of autoimmune diseases.

Invariant T cells can also promote rapid Th1 immune responses and anti-tumor responses. Invariant T cells, which comprise a major fraction of the T cells in murine liver, can be stimulated by IL-12 to become active cytotoxic T cells and protect against liver metastases in tumor models. This conclusion was confirmed genetically through the generation of Jα281 knockout mice, which do not express the invariant Vα14-Jα281 TCR. These mice had markedly diminished numbers of invariant T cells and could not mediate IL-12 induced tumor rejection. Other studies showed that IL-12 administration no longer induced an early IFN-γ response in the spleen and liver of CD1d knockout mice, which are invariant T cell deficient. In addition, data from human patients shows fewer invariant NK T cells and reduced Th1-like responses in patients with advanced cancer. The anti-tumor response of activated invariant T cells could be partially mediated by their CD1d specific cytotoxicity and NK/LAK cell-like toxicity. Other regulatory functions of invariant T cells, possibly through cytokine production or interactions with antigen presenting cells (APCs), may also play important roles in anti-tumor immune responses.

Invariant T cells may also have a role in the pathogenesis of spontaneous abortion. Stimulation of decidual invariant T cells in mice by administration of a ligand for invariant T cells provoked abortion in pregnant mice. The perforin-dependent killing and production of IFN-γ and tumor necrosis factor-α by the invariant T cells were required for this induction of abortion.

In contrast to human peripheral blood in which invariant T cells are the major CD1d-reactive subpopulation, human and mouse bone marrow and human liver have T cell populations dominated by CD1d-reactive noninvariant T cells using diverse TCRs which can also produce a large amount of IL-4 and IFN-γ. These CD1d-reactive noninvariant T cells can be either NK or non-NK T cells, and they function similarly to CD1d-reactive invariant T cells. The CD1d-reactive noninvariant T cells in bone marrow may have a role in suppressing graft versus host disease, and both populations may enhance graft versus leukemia responses. In the liver, these T cells may protect against infections, such as Hepatitis C infections, but may also cause damage due to their Th1 response. Additionally, we found that CD1d-reactive NK T cells are critical for immune tolerance to antigens in the anterior chamber of the eye, an immune privileged site (Sonoda et al., supra). Such mechanisms may also be important in the maintenance of peripheral tolerance.

Parasitic glycosyl-phosphatidylinositols derived from *Plasmodium, Trypanosoma*, or *Leishmania* have been recently shown to stimulate murine CD1d-reactive invariant Vα14 NK T cells. In addition, an α-galactosylceramide (α-GalCer) lipid, which was isolated from marine sponge in a screen for anti-tumor activity, is a CD1d-presented antigen. α-GalCer is an example of an agent which can be used to expand human CD1d-reactive invariant T cells from umbilical cord or peripheral blood samples that are first enriched for invariant T cells by purification using an anti-Vα24 antibody. The enriched $V\alpha24^+$ cells are cocultured in the presence of α-GalCer and purified antigen-presenting cells (APCs). However, it would be desirable in a clinical setting to use a simpler method for enhancing protective immune responses that does not require the modulation of CD1-reactive T cells.

Thus, there exists a need to specifically modulate the immune system for the prevention and treatment of diseases and disorders such as diabetes, autoimmune diseases, infections, allergies, asthma, inflammatory conditions, spontaneous abortion, pregnancy, graft versus host disease, and cancers.

SUMMARY OF THE INVENTION

We have developed novel methods for the prevention, stabilization, or treatment of a variety of diseases including infectious and autoimmune diseases and cancers. These methods involve administering one or more anti-CD1 antibodies to a mammal in an amount sufficient to modulate the activity or number of antigen-presenting cells (APCs).

Accordingly, in a first aspect, the invention provides a method of preventing, stabilizing, or treating an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer in a mammal (e.g., a non-rodent mammal or a human). This method involves administering to the mammal one or more anti-CD1 antibodies or antibody fragments in an amount sufficient to prevent, stabilize, or treat the condition. In various embodiments, the method increases the activity or number of one or more APCs by at least 20, 30, 40, 50, 60, 80, 90, 100, 200, 500, or even 1,000%. In various embodiments, the anti-CD1 antibody is administered at a dosage level that allows retention of at least 20, 30, 40, 50, 60, 80, 90, or 100% of the activity of CD1-reactive T cells (e.g., CD1d-reactive T cells, NK T cells, invariant T cells, or $J\alpha Q^+$ T cells) in the mammal relative to the corresponding level of T cell activity in the mammal before administration of the anti-CD1 antibody, or relative to the corresponding level of T cell activity in an untreated mammal. In some embodiments, the method increases the activity of CD1-reactive T cells by at least 20, 30, 40, 50, 60, 80, 90, 100, 200, 500, or even 1,000%. In other embodiments, the method decreases the amount of IL-12, TNF, or IFN-γ. In some embodiments, the method decreases the amount of IL-12, TNF, and IFN-γ. Desirably, the decrease in the amount of one or more of these cytokines is at least 10, 20, 30, 40, 50, 60, 80, 90, or 95%. In some embodiments, the method increases the amount of TGF-β, IL-12, IL-1α, or IL-10. Desirably, the increase in the amount of this cytokine is at least 10, 20, 30, 40, 50, 60, 80, 90, 100, 200, 500, or even 1,000%. In particular embodiments, the method increases the amount of TGF-β, IL-10, and/or IL-12. In still other embodiments, the method decreases the amount of IL-12, TNF, or IFN-γ, and increases the amount of TGF-β and/or IL-10. In some embodiments, the condition is an autoimmune disease other than lupus or a bacterial infection other than a *listeria* infection.

In another aspect, the invention provides a method of preventing, stabilizing, or treating APC pathogenesis in a mammal (e.g., a non-rodent mammal or a human). This method involves administering to the mammal one or more anti-CD1 antibodies or antibody fragments in an amount sufficient to reduce the number or activity of at least one APC. In various embodiments, the method decreases the activity or number of one or more APCs by at least 20, 30, 40, 50, 60, 80, 90, 95 or 100%. In another desirable embodiment, the antibody or antibody combination is covalently linked to a toxin, a radiolabel, or a molecule which targets host defensive or catabolic processes toward the cells. In one desirable embodiment, one or more cytokines are also administered to the animal. In another embodiment, the APC pathogenesis is an autoimmune pathology such as a response to a viral infection, such as a Hepatitis infection, picornarirus infection, polio infection, or coxsacchie infection.

In another related aspect, the invention provides another method of preventing, stabilizing, or treating an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer in a mammal (e.g., a non-rodent mammal or a human). This method involves administering to the mammal one or more APCs (e.g., dendritic cells) that have been contacted with one or more anti-CD1 antibodies or antibody fragments. The APCs are administered in an amount sufficient to prevent, stabilize, or treat the condition. In a desirable embodiment, the APCs are isolated from a mammal, contacted with an anti-CD1 antibody, optionally purified, and then re-administered to the same mammal. In yet another desirable embodiment, the antibody or antibody combination is administered to an APC derived from the mammal in vitro, followed by re-infusion of the cell. Desirably, other agents which may potentiate this activity are administered in vitro or in vivo. In some embodiments, an anti-CD1 antibody is also administered to the mammal.

Anti-CD1 antibodies can also be used to increase the immune response to a vaccine that is administered for the treatment or prevention of an infection.

Accordingly, in one such aspect, the invention features a method of preventing, stabilizing, or treating an infection in a mammal (e.g., a non-rodent mammal or a human). This method involves administering to the mammal an antigen from an infectious agent and one or more anti-CD1 antibodies or antibody fragments in an amount sufficient to prevent, stabilize, or treat the infection. Exemplary antigens include one or more proteins, peptides, lipids, carbohydrates, nucleic acids, small molecules, or intact infectious agents such as bacteria, viruses, or yeast. Other examples of antigens include any commercially available vaccine, such as an HIV, ebola, or small pox vaccine. The antigen may be administered to the mammal before, during, or after the administration of the anti-CD1 antibody.

In another aspect, the invention features a pharmaceutical composition that includes an anti-CD1 antibody and (i) an antigen from an infectious agent, (ii) a vaccine, or (iii) an adjuvant in any pharmaceutically acceptable form, including isomers such as salts, solvates, and polymorphs thereof. In various embodiments, the composition also includes a pharmaceutically acceptable carrier or diluent and/or an adjuvant. In some embodiments, the antigen is inactivated using standard methods such as heat or chemical (e.g., formaldehyde) inactivation. Exemplary antigens include proteins, peptides, lipids, carbohydrates, nucleic acids, small molecules, or intact infectious agents such as a bacteria, viruses, or yeast.

The invention also features methods for increasing the activity or number of APCs in vitro or in vivo. In one such aspect, the invention provides a method of increasing the production or secretion of a cytokine by an APC. This method involves administering to an APC one or more anti-CD1 antibodies or antibody fragments in an amount sufficient to increase the production or secretion of a cytokine by the APC. In various embodiments, the method increases the secretion of one or more of the following cytokines by at least 20, 30, 40, 50, 60, 80, 90, 100, 200, 500, or even 1,000%: IL-1α, IL-2, IL-4, IL-7, IL-10, IL-12, IL-13, IL-15, IL-18, IFN-α/β, IFN-γ, or GM-CSF. In particular embodiments, the secretion of IL-12 by dendritic cells increases by at least 50, 60, 80, 90, 100, 200, 500, or even 1,000%. The APC may be in vitro or in vivo (e.g., in a mammal such as a human). In some embodiments, the APC is in or from a mammal diagnosed with, or at increased risk for, a disease, disorder, or infection selected from the group consisting of: an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer. In some embodiments, the autoimmune disease is a disease other than lupus, or the bacterial infection is an infection other than a *listeria* infection.

In desirable embodiments of any aspect of the invention, the antibody or antibody combination is administered to the animal intraarticularly, intralesionally, orally, intramuscularly, intravenously, subcutaneously, or intraperitoneally. In another desirable embodiment, the antibody or antibody combination is administered with a pharmaceutically suitable carrier. Desirably, the antibody or antibody combination is administered to the animal in a dose that is less than 20, 15, 10, 5, 4, or 1 mg/kg. In some embodiments, the dose falls within one of the following ranges: 0.1 to 10 mg/kg, 0.1 to 0.4 mg/kg, 0.1 to 1 mg/kg, or 1 to 4 mg/kg, inclusive.

In various embodiments of any aspect of the invention, the anti-CD1 antibody is administered at a dosage level that allows retention of at least 20, 30, 40, 50, 60, 80, 90, or 100% of the activity of CD1-reactive T cells (e.g., CD1d-reactive T cells, NK T cells, invariant T cells, or JαQ$^+$ T cells) in the mammal relative to the corresponding level of T cell activity in the mammal before administration of the anti-CD1 antibody, or relative to the corresponding level of T cell activity in an untreated mammal. In other embodiments, the method decreases the amount of IL-12, TNF, and/or IFN-γ and/or increases the amount of TGF-β and/or IL-10. Desirably, the decrease in the amount of one or more of these cytokines is at least 10, 20, 30, 40, 50, 60, 80, 90, or 95%. In some embodiments, the method increases the amount of TGF-β, IL-1α, IL-10, or IL-12 by at least 10, 20, 30, 40, 50, 60, 80, 90, 100, 200, 500, or even 1,000%. In particular embodiments, the method increases the amount of IL-12 produced by dendritic cells by at least 10, 20, 30, 40, 50, 60, 80, 90, 100, 200, 500, or even 1,000%.

In another desirable embodiment, a cell type or other agent such as an anti-microbial, chemotherapeutic, immune suppressive, or immunomodulatory compound which works in concert with the antibodies is also administered to the mammal. In various embodiments, one or more cytokines (e.g., IL-2, IL-4, IL-7, IL-10, IL-12, IL-13, IL-15, IL-18, IFN-α/β, IFN-γ, or GM-CSF) are also administered to the mammal. Desirably, the cytokine is administered to the mammal before, during, or after the anti-CD1 antibody is administered to the mammal. In desirable embodiments, the cytokine is administered intramuscularly, intravenously, intraarticularly, intralesionally, subcutaneously, or by any other route sufficient to provide a dose adequate to modulate the activity of an APC or a T cell (e.g., a CD1-reactive T cell). Desirably, the cytokine alters the ratio of Th1/Th2/immune deviation response by the contacted T cells. In some embodiments of methods of treating or preventing an undesired immune responses (e.g., autoimmunity, transplant rejection, graft-versus-host disease, allergy, asthma, fetal rejection, or immune complex diseases) an anti-CD1 antibody is administered in combination with an agent (e.g., TGF-β or IL-4) which alone or in combination promotes an anti-inflammatory response through an APC. In some embodiments, an antigen such as a lipid or glycosyl-phosphatidylinositol antigen from an infectious pathogen, an antigen from a cancerous cell, a self-lipid, α-galactosylceramide, or an antigen other than α-galactosylceramide is administered to the mammal. In various embodiments, an anti-CD1 antibody and an antigen such as a lipid or glycosyl-phosphatidylinositol antigen from an infectious pathogen, an antigen from a cancerous cell, a self-lipid, α-galactosylceramide, or an antigen other than α-galactosylceramide is contacted with the APC ex vivo, and the cell is later introduced into a mammal. In other embodiments, an anti-CD40 antibody is also administered to the mammal.

In desirable embodiments, the anti-CD1 antibody binds and activates APCs expressing CD1d. In some embodiments, the anti-CD1 antibody only substantially activates APCs expressing one CD1 molecule (e.g., only activating APCs expressing one CD1 molecule selected from the group consisting of CD1a, CD1b, CD1c, and CD1d). For example, the antibody may activate APCs expressing CD1d by at least 2, 5, or 10 fold more than APCs expressing CD1a, CD1b, or CD1c. Desirable APCs include CD1-expressing monocytes, macrophages, various dendritic cells, and B cells. Other APCs include Langerhan cells, epithelial cells, and mesenchymal cells.

In a further embodiment of any of the above aspects, administering an anti-CD1 antibody includes contacting an in-dwelling device with the antibody prior to, concurrent with, or following the administration of the in-dwelling device to a patient. In-dwelling devices include, but are not limited to, surgical implants, prosthetic devices, and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

In desirable embodiments, the viral infection relevant to the methods of the invention is an infection by one or more of the following viruses: diabetogenic encephalomyocarditis virus, Hepatitis, picornarirus, polio, HIV, coxsacchie, herpes simplex, St. Louis encephalitis, Epstein-Barr, myxovirus, JC, coxsakievirus B, togavirus, measles, paramyxovirus, echovirus, bunyavirus, cytomegalovirus, varicella-zoster, mumps, equine encephalitis, lymphocytic choriomeningitis, rabies, simian virus 40, human polyoma virus, parvovirus, papilloma virus, primate adenovirus, and/or BK.

In the desirable embodiments, the bacterial infection is due to one or more of the following bacteria: *Chlamydophilapneumoniae, C. psittaci, C. abortus, Chlamydia trachomatis, Simkania negevensis, Parachlamydia acanthainoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacterfetus, C. jejuni, C. coli, Borrelia burgdorferi, V. cholerae, V parahaemolyticus, Legionella pneumophila, Listeria monocytogenes, Neisseria gonorrhea, N. meningitidis, Kingella dentrificans, K kingae, K. oralis, Moraxella catarrhalis, M atlantae, M lacunata, M. nonliquefaciens, M osloensis, M. phenylpyruvica, Gardnerella vaginalis, Bacteroides fragilis, Bacteroides distasonis, Bacteroides* 3452A homology group, *Bacteroides vulgatus, B. ovalus, B. thetaiotaomicron, B. uniform is, B. eggerthii, B. splanchnicus, Clostridium difficile, Mycobacterium tuberculosis, M. avium, M. intracellulare, M leprae, C. diphtheriae, C ulcerans, C. accolens, C. afermentans, C. amycolatum, C. argentorense, C. auris, C. bovis, C. confusum, C coyleae, C. durum, C. falsenii, C. glucuronolyticum, C. itnitans, C. jeikeium, C. kutscheri, C. kroppenstedtii, C. lipophilum, C. macginleyi, C. matruchoti, C. mucifaciens, C. pilosum, C. propinquum, C. renale, C riegelii, C. sanguinis, C. singulare, C. striatum, C. sundsvallense, C. thomssenii, C urealyticum, C. xerosis, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epiderinidis, S. saprophyticus, S. internedius, S. hyicus, S. haemolyticus, S. hominis*, and/or *S. saccharolyticus*. In some embodiments, the bacterial infection is an infection by a bacteria other than *listeria*. Desirably, an anti-CD1 antibody is administered in an amount sufficient to prevent, stabilize, or inhibit the growth of a pathogen or to kill the pathogen.

In other embodiments, the autoimmune disease is type 1 diabetes. In some embodiments, the autoimmune disease is a disease other than lupus. In yet other embodiments, the disease treated or prevented using the methods of the invention is a condition (e.g., an autoimmune disease such as diabetes or multiple sclerosis) in which downregulation of IL-12 production (e.g., a reduction of at least 25, 50, 75, or 90%) is beneficial.

Desirably, the mammal is a non-rodent mammal or a human. Other desirable animals include mammals of laboratory or veterinary interest such as mice, rats, rabbits, pigs, goats, cattle, sheep, and horses.

It should be understood that each of the aspects of the invention apply equally to the antibodies, bifunctional antibodies, fragments of antibodies, and derivatives of antibodies of the invention. In various embodiments, the antibodies in an antibody combination of the invention are simultaneously or sequentially administered to an mammal for the treatment stabilization, or prevention of a disease or condition.

It is also contemplated that other ligands for CD1 such as polymers of ceramide or other multimeric antigens such as multimeric lipids that cross-link CD1 on APCs can be used any of the methods or pharmaceutical compositions of the invention instead of, or in addition to, an anti-CD1 antibody.

By "anti-CD1 antibody" is meant an antibody which recognizes and binds CD1 (e.g., CD1a, CD1b, CD1c, and/or CD1d), but which does not substantially recognize and bind other molecules in a sample, e.g., a biological sample, which naturally includes other protein or cells. The signal in a standard ELISA assay for the binding of the antibody to CD1 expressed on a cell is desirably at least 2, 3, 4, 5, 10, 15, 20, 30, 40, 50, 60, 70, 80, 90, 100, 150, 200, or 500 times greater than that for the binding to a control cell that is not a APC cell or to a control cell that does not express CD1. Humanized or other species forms of the antibody may be generated using standard techniques. The antibody may be polyclonal or monoclonal.

Desirably, the antibody is "purified," meaning it has been separated from other components that naturally accompany it. Typically, the antibody is substantially pure when it is at least 50%, by weight, free from proteins, antibodies, and naturally-occurring organic molecules with which it is naturally associated. Desirably, the antibody is at least 75%, more desirably, at least 90%, and most desirably, at least 99%, by weight, pure. A substantially pure anti-CD1 antibody may be obtained, for example, by using a method of the present invention to immunize a mammal for the generation of the antibody, by construction of hybridoma secreting the antibody, by chemically synthesizing the antibody, or by separation of the antibody from natural sources. Purity can be assayed by any appropriate method, as described below for the isolation of antibodies.

By "CD1" is meant a CD1 molecule such as CD1a, CD1b, CD1c, or CD1d. Desirably, the CD1 molecule has an amino acid sequence that is at least 60, 70, 80, 90, 95, or 100% identical to human CD1a, CD1b, CD1c, or CD1d (Balk et al., Proc Natl Acad Sci USA 86(1):252-6, 1989; Martin et al., Proc Natl Acad Sci USA 84(24):9189-93, 1987).

By "fragment" is meant a polypeptide having a region of consecutive amino acids that is identical to the corresponding region of an antibody of the invention. The fragment has the ability to bind, activate, and/or expand APCs ex vivo or in vivo, as determined using the assays described herein. Desirably, the number, activity, or purity of the expanded cells is at least 20, 40, 60, 80, or 90% of that produced by a full-length antibody, as measured using the assays provided herein. Desirably, the binding of the fragment to CD1 or to an APC is at least 20, 40, 60, 80, or 90% of that of a full-length antibody.

By "derivative" is meant an antibody or fragment that is modified chemically or through gene fusion technology or chemical synthesis so that it is covalently linked to a toxin, therapeutically active compound, enzyme, cytokine, radiolabel, fluorescent label, or affinity tag. The covalently linked group can be attached to the amino terminus, carboxy terminus, between the amino and carboxy termini, or to a side chain of an amino acid in the antibody or fragment. By "affinity tag" is meant a peptide, protein, or compound that binds another peptide, protein, or compound. In a desirable embodiment, the affinity tag is used for purification or immobilization of the derivative. In another desirable embodiment, the affinity tag or toxin is used to target the antibody or fragment to a specific cell, tissue, or organ system in vivo. In still another desirable embodiment, the fluorescent or radiolabel is used for imaging of the derivative. In yet another desirable embodiment, the therapeutically active compound or radiolabel is used for the treatment or prevention of a disease or disorder. In another embodiment, the derivative or fragment of an antibody of the invention has increased stability or increased solubility compared to the antibody. It is also contemplated that the antibody, fragment, or derivative of the invention may be bound non-covalently to another antibody covalently linked to a toxin, therapeutically active compound, enzyme, cytokine, radiolabel, fluorescent label, magnetic label, or affinity tag.

By "humanized" is meant alteration of the amino acid sequence of an antibody so that fewer antibodies and/or immune responses are elicited against the humanized antibody when it is administered to a human. For example, the constant region of the antibody may be replaced with the constant region of a human antibody. For the use of the antibody in a mammal other than a human, an antibody of the invention may be converted to that species format.

By "bifunctional antibody" is meant an antibody that includes an antibody or a fragment of an antibody covalently linked to another antibody or another fragment of an antibody. Desirably, both antibodies or fragments bind to different CD1 epitopes or different proteins expressed on the same APC. Desirably, the antibody binds CD1 a, CD 1b, CD1c, CD19, CD20, CD22, CD23, CD38, CD40, CD44, CD62L, CD69, CD83, MHC molecules, an antigen receptor, a Fc receptor, or a cytokine receptor component.

By "invariant T cell" is meant a T cell having a CD1d-reactive invariant T cell antigen receptor. By "human CD1d-reactive invariant T cell antigen receptor" is meant a T cell antigen receptor that recognizes CD1d and has an alpha chain that is generated from a rearrangement between V$\alpha$24 and J$\alpha$Q that produces little or no N-region diversity (Kent et al., Human Immunology 60:1080-1089, 1999). In mice, the invariant TCR-a chain is generated from a rearrangement between V$\alpha$14 and J$\alpha$281 that produces little or no N-region diversity. The equivalent rearrangement may occur in other mammals (e.g., rats) and in birds. Although human invariant TCR-a chain pairs preferentially with V$\beta$11, it can pair with other V$\beta$s. The human CD1d-reactive invariant T cell antigen receptor recognizes CD1d, but not the closely related CD1a, CD1b, or CD1c family members (Exley et al., J. Exp. Med. 186(1):109-120, 1997).

By "treating, stabilizing, or preventing a disease or disorder" is meant, preventing an initial or subsequent occurrence of a disease or disorder, increasing the disease-free survival time between the disappearance of a disease or disorder and its reoccurrence, reducing an adverse symptom associated with a disease or disorder, or inhibiting or stabilizing the progression of a disease or disorder. Desirably, at least 20, 40, 60, 80, 90, or 95% of the treated subjects have a complete remission in which all evidence of the disease disappears. In another embodiment, the length of time a patient survives after being diagnosed with a disease and treated with an anti-CD1 antibody is at least 20, 40, 60, 80, 100, 200, or even 500% greater than (i) the average amount of time an untreated patient survives or (ii) the average amount of time a patient treated with another therapy survives.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing an adverse symptom associated with a tumor. In various embodiments, the percent of cancerous cells surviving the treatment is at least 20, 40, 60, 80, or 100% lower than the initial number of cancerous cells, as measured using any standard assay. Desirably, the decrease in the number of cancerous cells induced by administration of a therapy of the invention is at least 2, 5, 10, 20, or 50-fold greater than the decrease in the number of non-cancerous cells. In yet another embodiment, the number of cancerous cells present after administration of an anti-CD1 antibody is at least 2, 5, 10, 20, or 50-fold lower than the number of cancerous cells present after administration of a vehicle control. Desirably, the methods of the present invention result in a decrease of 20, 40, 60, 80, or 100% in the size of a tumor as determined using standard methods. Desirably, at least 20, 40, 60, 80, 90, or 95% of the treated subjects have a complete remission in which all evidence of the cancer disappears. Desirably, the cancer does not reappear or reappears after at least 5, 10, 15, or 20 years. In another embodiment, the length of time a patient survives after being diagnosed with cancer and treated with a therapy of the invention is at least 20, 40, 60, 80, 100, 200, or even 500% greater than (i) the average amount of time an untreated patient survives or (ii) the average amount of time a patient treated with another therapy survives.

By "bacterial infection" is meant the invasion of a host mammal by pathogenic bacteria. For example, the infection may include the excessive growth of bacteria that are normally present in or on the body of a mammal or growth of bacteria that are not normally present in or on the mammal. More generally, a bacterial infection can be any situation in which the presence of a bacterial population(s) is damaging to a host mammal. Thus, a mammal is "suffering" from a bacterial infection when an excessive amount of a bacterial population is present in or on the mammal's body, or when the presence of a bacterial population(s) is damaging the cells or other tissue of the mammal. In one embodiment, the number of a particular genus or species of bacteria is at least 2, 4, 6, or 8 times the number normally found in the mammal. The bacterial infection may be due to gram positive and/or gram negative bacteria.

By "viral infection" is meant the invasion of a host mammal by a virus. A viral infection can be any situation in which the presence of a viral population(s) is damaging to a host mammal. Thus, a mammal is "suffering" from a viral infection when an excessive amount of a viral population is present in or on the mammal's body, or when the presence of a viral population(s) is damaging to the cells or other tissue of the mammal.

By "APC pathogenesis" is meant a disease or disorder that is caused or exacerbated by an activity of an APC, such as its antibody, cytokine, or growth factor production. APC pathogenesis may include, for example, an autoimmune pathology, such as a response to a hepatitis infection.

By "autoimmune disease" is meant a disease in which an immune system response is generated against self epitopes. Some examples of autoimmune diseases include insulin dependent diabetes mellitus, rheumatoid arthritis, pemphigus vulgaris, multiple sclerosis, and myasthenia gravis.

By "increasing the number, differentiation, or activity of APCs" is meant stimulating the activity, differentiation, or expansion of these cells by administering an anti-CD1 antibody. Desirably, the number of APCs belonging to the subpopulation that are present after this administration is at least 2, 3, 4, 5, 10, 15, 20, 30, 40, 50, 70, 90, 150, or 500 fold greater than the number of these cells present after administration of a control antibody. In other desirable embodiments, the amount of antibody, cytokines, or growth factors produced by APCs increases by at least 25, 50, 75, 100, 200, 500, or even 1000%. In other embodiments, the percentage of B cells that secrete antibody increases by at least 25, 50, 75, 100, 200, 500, or 1000%. In still other desirable embodiments, the proliferation of APCs increases by at least 25, 50, 75, 100, 200, 500, or 1000%, as measured using a standard assay (e.g., an assay for $^{3}$H-thymidine incorporation) to measure the rate of DNA synthesis. Desirably, the number of monocytes that have differentiated into macrophages increases by at least 25, 50, 75, 100, 200, 500, or even 1000%. Activated macrophages can be assayed using standard methods, such as those that measure the ability of macrophages to kill microorganisms or tumor cells. Exemplary standard assays for measuring APC activity, differentiation, and proliferation can be found in, for example, Abbas et al. (Cellular and Molecular Immunology, 2$^{nd}$ ed., W.B. Saunders Company, Philadelphia, 1994; Current Protocols in Immunology, Wiley, 1996 and later versions).

By "preferentially modulating the expansion or activation of at least one CD-1 expressing APC" is meant inducing or inhibiting the expansion or activation of a CD-1 expressing APC such as a monocyte, macrophage, dendritic cell, and/or B cell. The induction of the expansion of these cell subpopulations may be measured using standard methods, as described above. The inhibition of the expansion of these cell subpopulations may be determined by comparing the number of cells belonging to the subpopulation after incubation with an anti-CD1 antibody compared to a control incubation without the antibody. Desirably, the number of cells belonging to the subpopulation present after incubation with the antibody is 2, 3, 4, 5, 10, 15, 20, 30, 40, 50, or 100 fold less than the number of these cells present after the corresponding control incubation. This inhibition of cell expansion may be useful in the prevention or treatment of APC pathogenesis. The induction or inhibition of the activation of a cell subpopulation may be assayed using standard procedures to measure the antibody, cytokine, or growth factor production or cytotoxicity of the cell subpopulation. Desirably, the increase or decrease in the antibody, cytokine, or growth factor production or cytotoxicity is at least 5, 10, 20, 20, 40, 50, 70, 90, or 100% of the activity of the control cell subpopulation incubated in the absence of the antibody. Desirably, the change in the size or activity of at least one cell subpopulation selected from the group consisting of monocytes, macrophages, dendritic cells, and B cells is least 2, 3, 4, 5, 10, 15, 20, 30, 40, 50, 70, 90, 150, or 500 times greater that the corresponding change in cells other than monocytes, macrophages, dendritic cells, or B cells or cells other than CD1d-expressing cells.

The present invention provides numerous advantages. For example, the use of an anti-CD1 antibody for the modulation of APCs eliminates the requirement for directly modulating CD1-reactive T cells, removing them as potential sources of variability and greatly simplifying the procedure for clinical trials. The present methods also have the advantage of requiring only a relatively small dose of anti-CD1 antibody to be administered to activate CD1-expressing APCs rather than requiring a relatively large dose of antibody to prevent most or all T-cells from interacting with CD1-expressing APCs.

Other features and advantages of the invention will be apparent from the following detailed description.

BRIEF DESCRIPTION OF THE DRAWINGS

FIGS. 26A-26D are graphs generated from a FACSCAN cytometer showing the presence of external CD1d on the cell surface of THP-1 cells.

DETAILED DESCRIPTION

Figure 1:
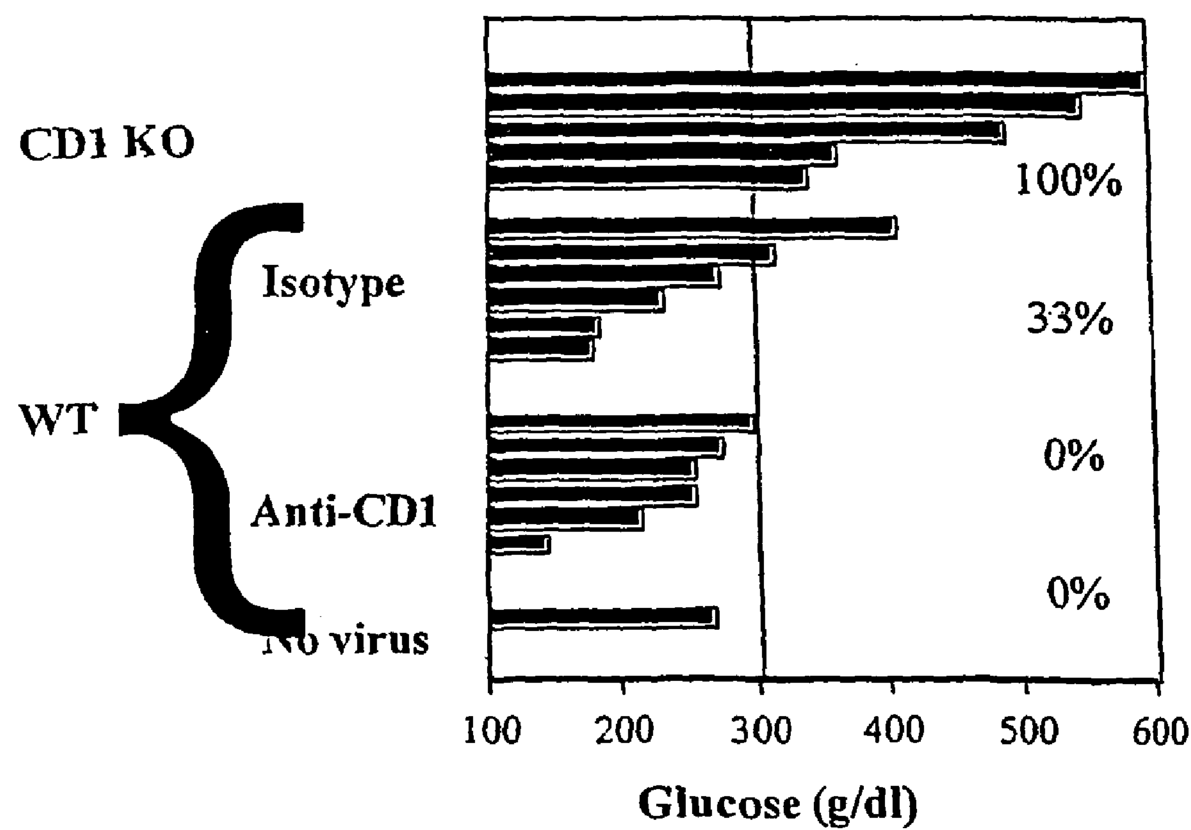
FIG. 1 is a graph showing the increased frequency of disease in CD1 knockout mice and protection against viral infection using an anti-CD1 monoclonal antibody. Mice were infected with EMCV-D and followed as described (Exley et al., Journal of Leukocyte Biology 69:713-718, 2001). Fifty mg of the anti-CD1 monoclonal antibody 3C11 or an isotype control monoclonal antibody was given one day prior to infection. A standard glucose tolerance test was used to determine the percentage of mice with diabetes. Mice with glucose levels greater than the level represented by the vertical line in the graph (~300 g/dl; which is the mean level of glucose for healthy mice plus 3 standard deviations were characterized as diabetic. The administration of the anti-CD1 antibody significantly decreased the incidence of diabetes.

We have made the surprising discovery that an anti-CD1 antibody can be used to directly activate antigen presenting cells (APCs; e.g., CD1-expressing monocytes, macrophages, dendritic cells, and B cells) without the need to directly modulate the activity of CD1-reactive T cells. For example, administration of an anti-CD1 antibody resulted in the production of therapeutic cytokines and protective responses in a viral model. In particular, anti-CD1 antibodies induced IL-12, IL-1α, and IL-10 and protected mice against lethal challenge in an acute viral infection model, the picornavirus EMCV. In vitro results also demonstrated that anti-CD1 antibodies are more potent than CD40 ligation in stimulation of monocytes for production of bioactive IL-12. CD1 antibodies can also synergize with antibodies such as anti-CD40 antibodies to stimulate monocytes in vitro. Even in the absence of anti-CD40 antibodies, anti-CD1 antibodies can activate dendritic cells to produce bioactive IL-12.

The generality of CD1 activation was confirmed using panels of CD1 antibodies. Several monoclonal antibodies to different CD1 epitopes activated the target cells. IFN-γ enhances sensitivity so that an anti-CD1 antibody alone activates APCs without the need for CD40 ligation.

Thus, anti-CD1 antibodies represent novel therapeutic approaches to optimizing protective responses without the need to directly modulate the activity of CD1-reactive T cells (e.g., without having to significantly or completely inhibit the binding of CD1-reactive T cells to CD1-expressing APCs). The present invention uses ligands for CD1 (e.g., antibodies) to directly bind and activate monocytes and other APCs, leading to production of therapeutic cytokines and by cell-contact to stimulation of protective responses. Anti-CD1 antibodies can be used for in vivo or alternately in vitro activation of APC followed by re-infusion to induce protective responses against viral, bacterial, yeast, and parasitic infectious diseases and cancer and to positively influence undesirable responses such as autoimmunity and allergic responses. The administration of anti-CD1 antibodies of the invention may be performed alone or in conjunction with the administration of other therapeutics, such as cytokines, tumor vaccines, or other antibodies reactive with APCs.

Anti-CD1 antibodies may be administered to a mammal, such as a human, for the prevention or treatment of autoimmune diseases, infectious diseases, allergies, asthma, inflammatory conditions, graft versus host disease, graft rejection, immunodeficiency disease, spontaneous abortion, pregnancy, or cancer. Anti-CD1 antibodies may be used to activate CD1-expressing APCs and thereby stimulate protective responses of CD1-reactive T cells. For example, reduced levels of certain T cells such as invariant NK T cells are found in prostate cancer, multiple sclerosis, HIV, and type 1 diabetes patients (WO 01/98357, published Dec. 27, 2001). Additionally, a reduced number of $V\alpha24^{+}$ $CD161^{+}$ T cells has been previously reported for melanoma patents (Kawano et al., Cancer Res. 59:5102, 1999); thus, the loss of invariant NK T cell function may be a general finding in advanced cancer.

In addition to, or instead of, administering an anti-CD1 antibody to a mammal, APCs that have been incubated in vitro with an anti-CD1 antibody can be administered to a mammal to increase the number of active APCs in the mammal. Desirably, the APCs are administered to the same mammal from which they were isolated.

Anti-CD1 antibodies may also be administered with any commercially available vaccine to enhance the immune response to an infection. Thus, anti-CD1antibodies can be used to increase the effectiveness of a vaccine for the prevention or treatment of an infection, such as a bacterial or viral infection.

Alternatively, antibodies that bind and inhibit the expansion or an activity of APCs, such as antibody or cytokine production, may be used to inhibit APC cell pathogenesis in a mammal. The immune response induced by infectious agents, such as Hepatitis viruses, can cause damage which may be minimized by the inhibition of these cells. Examples of some of the antibodies that may inhibit these cells include monovalent or Fab molecules or antibodies that are conjugated to a toxin or radiolabel that damages the cells upon binding of the antibody to the cells.

In addition to administering an anti-CD1 antibody or ex vivo expanded APCs, cytokines can also be administered to a mammal to further modulate the immune system. Using a cytoline, such as IL-12, IL-15, or IL-18, which is known to bias T cells towards Th1 responses is expected to increase the effectiveness of the present methods in the prevention or treatment of cancer, infectious disease, allergies, asthma, pregnancy, and inflammation. Alternatively, any other cytokine, such as IL-2, IL-4, IL-7, IL-10, IL-12, IL-13, IL-15, IL-18, IFN-α/β, IFN-γ, and GM-CSF, may be used to bias the T cells towards Th2 responses for the prevention or treatment of autoimmune diseases and graft versus host disease for which Th2 responses are protective. Alternatively, the cytoline may be used to bias the T cells away from Th1 and Th2 responses and towards immune deviation responses which may contribute to the maintenance of pregnancy. Immune deviation responses include the suppression of an ongoing immune response, such as a response at a immune-privileged site. TGF-β and IL-10 are examples of cytokines that may participate in immune deviation responses (Sonoda et al., supra).

The following examples are to illustrate the invention. They are not meant to limit the invention in any way.

EXAMPLE 1

Generation of anti-CD1 Antibodies

The generation of the 3C11 and 51.1 anti-CD1 antibodies has been described previously (see, for example, Bleicher et al., Science 250:679-682, 1990; Exley, Immunology 100:37-47, 2000; Kasinrerk et al., J Immunol 150(2):579-84, 1993; Dezutter-Dambuyant et al., Res Immunol 140(4):377-90, 1989; Kahn-Perles et al., J. Immunol. 134(3):1759-65, 1985; Porcelli et al., Nature 241(6241):447-50, 1989).

The 3C11 monoclonal antibody used in the experiments described herein was obtained from Dr. Steven Porcelli (formerly at Brigham & Women's Hospital, Mass.; now at Einstein College of Medicine, NY), who generated the antibody using antigen provided by Dr. Steven Balk. Additionally, the 1B1 anti-mouse CD1 monoclonal antibody is commercially available from Pharmingen.

For the production of additional anti-CD1 antibodies and hybridomas, a peptide from CD1, the entire CD1 protein, or APCs can be used. For example, an antigenic peptide is coupled to a carrier (e.g., a keyhole limpet hemocyanin carrier) and administered to an animal (e.g., a laboratory animal or an animal of veterinary interest) in one or more doses. Desirable routes of administration include intraperitoneally, intramuscular, intradermal, and subcutaneous. The dose and frequency of administration can be determined using standard procedures. Examples of mammals that may be used for the production of antibodies include mice, rats, rabbits, pigs, goats, sheep, horses, and cattle. Examples of birds that may be used include chickens and turkeys. The host animals may be wild-type animals, or they may be animals that have a reduced level or that lack CD1 or APCs. Other animals that may be used include animals that naturally, through genetic modification, or depletion lack CD1 or APCs. Any other animal that is capable of producing antibodies may also be used for the production of antibodies. If desired, the same peptide, another CD1 peptide, full-length CD1, or APCs may be administered as booster injections. Serum from the animal is tested for antibodies that bind the CD1 peptide or APC using a standard ELISA assay. Hybridomas are generated from seropositive animal spleens using standard techniques. ELISA positive hybridoma wells are further tested by FACS to compare binding of the antibodies to CD1 or APCs versus negative controls. Cells producing antibodies that bind CD1 or APCs but not the negative controls are cloned and fused to immune spleen cells using standard techniques. A group of hybridomas secreting monoclonal antibodies that specifically recognize CD1 (e.g., CD1d) are then identified using the ELISA assay. To generate antibodies that enhance production of IL-12 by THP-1 cells, hybridomas from animals desirably immunized with an APC or a synthetic antigen may be screened for the ability to simulate APC responses such as IL-12 or TGF-β production by measuring the activity or cytokine levels in the supernatants of the hybridomas. These stable monoclonal antibody secreting hybridomas clones may be used by one skilled in the art for the production and purification of clinical trial quality and quantity of these monoclonal antibody reagents.

Anti-CD1 antibodies can be purified from antiserum, ascites fluid, or hybridomas supernatant by one skilled in the art using standard techniques such as those described by Ausubel et al. (Current Protocols in Molecular Biology, volume 2, p. 11.13.1-11.13.3, John Wiley & Sons, 1995). The antibody is desirably at least 2, 5, or 10 times as pure as the starting material, as measured using polyacrylamide gel electrophoresis, column chromatography, optical density, HPLC analysis, or western analysis to detect a reduction in the amount of contaminating proteins or ELISA to detect an increase in specific activity for binding to CD1 or APCs.

The resulting antibodies may be used for clinical applications involving other animals of the same genus or species as the host animal used for antibody production. Additionally, the antibodies of the invention may be used in applications involving animals of a different genus as the host animal. For example, antibodies that are produced in bovines may be used for the treatment or prevention of disease in other bovines or in other mammals, such as humans.

EXAMPLE 2

Prevention and Treatment of Viral Infection using anti-CD1 Antibodies

The picornavirus, diabetogenic encephalomyocarditis virus (EMCV-D), causes lethal, acute disease in young male mice of appropriate strains. Female and older male mice are resistant. The severity of EMCV-D-induced disease varies in different genetic backgrounds, BALB/c being most sensitive and C57/B16 being most resistant. Contributions of NK cells, macrophages, and T cells to responses against various EMCV strains also vary in different strains. EMCV-D-induced disease can be measured by hind-limb paralysis (a manifestation of encephalitis) and glucose-tolerance testing (diabetes), reflecting acute, cytopathic effects of the virus on neuronal cells and islet cells, respectively. A further manifestation of EMCV-D infection is myocarditis. EMCV induced myocarditis involves limited, direct, viral damage in conjunction with extensive mononuclearcell infiltration.

To determine the ability of anti-CD1 antibodies to protect against viral infection, mice were administered one or more anti-CD1 antibodies prior to infection with EMCV-D (Exley et al., Journal of Leukocyte Biology 69:713-718, 2001). Briefly, BALB/c-backcrossed, CD1d-KO mice (F8), and Ja281-KO mice (F 10) were administered fifty microgram of anti-CD1 monoclonal antibody 3C11, anti-CD1 monoclonal antibodies 3C11 and 1B1, or isotype control antibody one day prior to viral infection (Smiley et al, Science 275:977-979, 1997; Cui et al., Science 278:1623-1626; 1997). Wild-type and knockout (1293C57/B16)F2 or BALB/c mice were infected intraperitoneally (i.p.) with 800 plaque-forming units (PFU) EMCV-D (Giron et al., Proc. Soc. Exp. Biol. Med. 173:328-331, 1983). The mice were then examined to determine the frequency of paralysis and diabetes. Paralysis score 1 denotes no paralysis; 2 denotes limp or partial use of one paw; 3 denotes one completely paralyzed hind paw; 4 denotes loss of two hind limbs; and 5 denotes paralysis of three or four paws. Glucose tolerance testing was performed by i.p. injection of 2 g/Kg glucose with blood collected into glucosidase inhibitor-treated tubes at one hour (Giron et al., supra). Organs were fixed for histology at this time.

Figure 2:
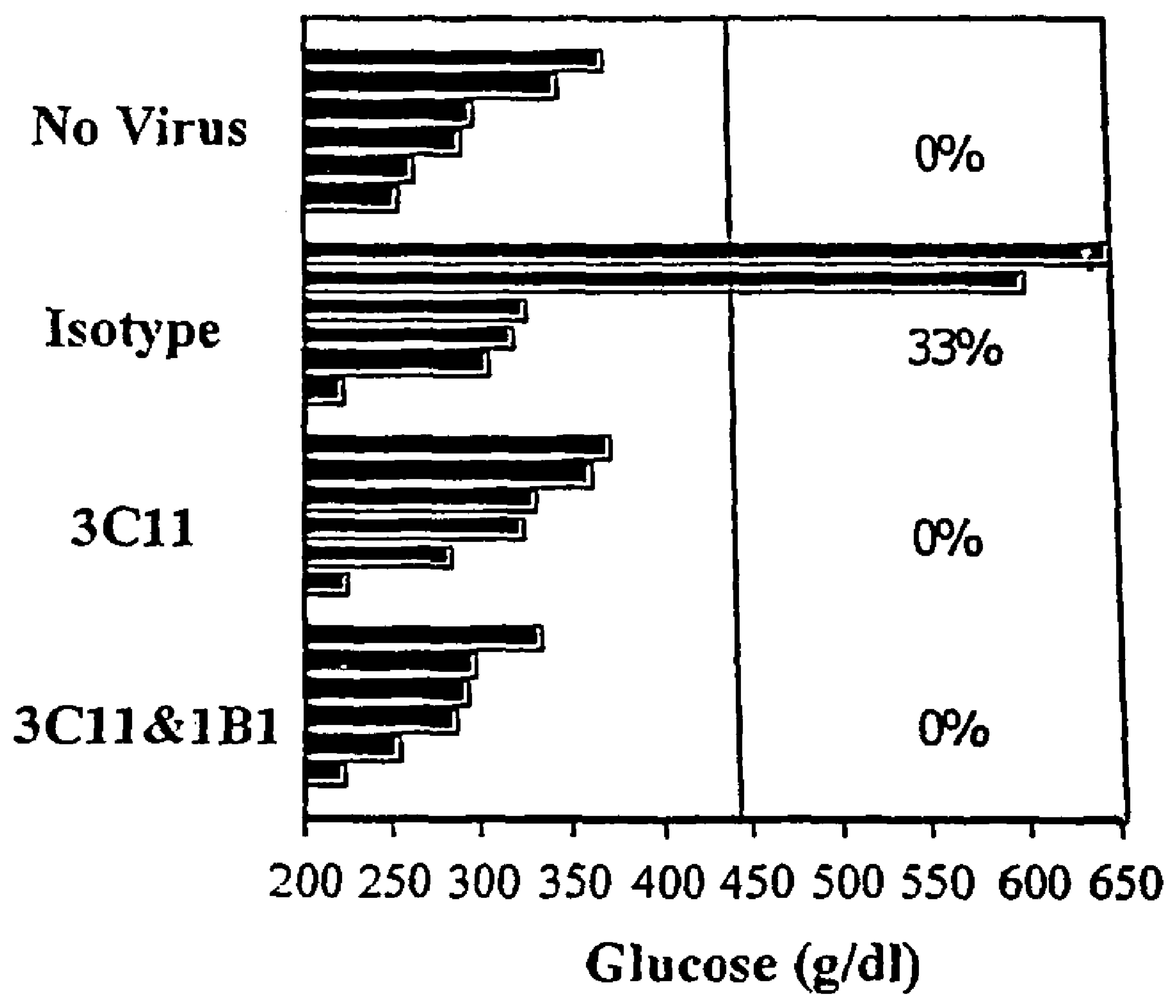
FIG. 2 is a graph showing protection against virus infection with an anti-CD1 monoclonal antibody. In an independent experiment from that described in FIG. 1, mice were infected with EMCV-D and followed as described (Exley et al., Journal of Leukocyte Biology 69:713-718, 2001). Fifty mg of 3C11 anti-CD1 monoclonal antibody, 3C11 and 1B1 (from PharmEngine) anti-CD1 monoclonal antibodies, or isotype control monoclonal antibodies were given one day prior to infection. Mice with glucose levels greater than the level represented by the vertical line in the graph were characterized as diabetic. The administration of one or both anti-CD1 antibodies significantly decreased the incidence of diabetes.
Figure 3:
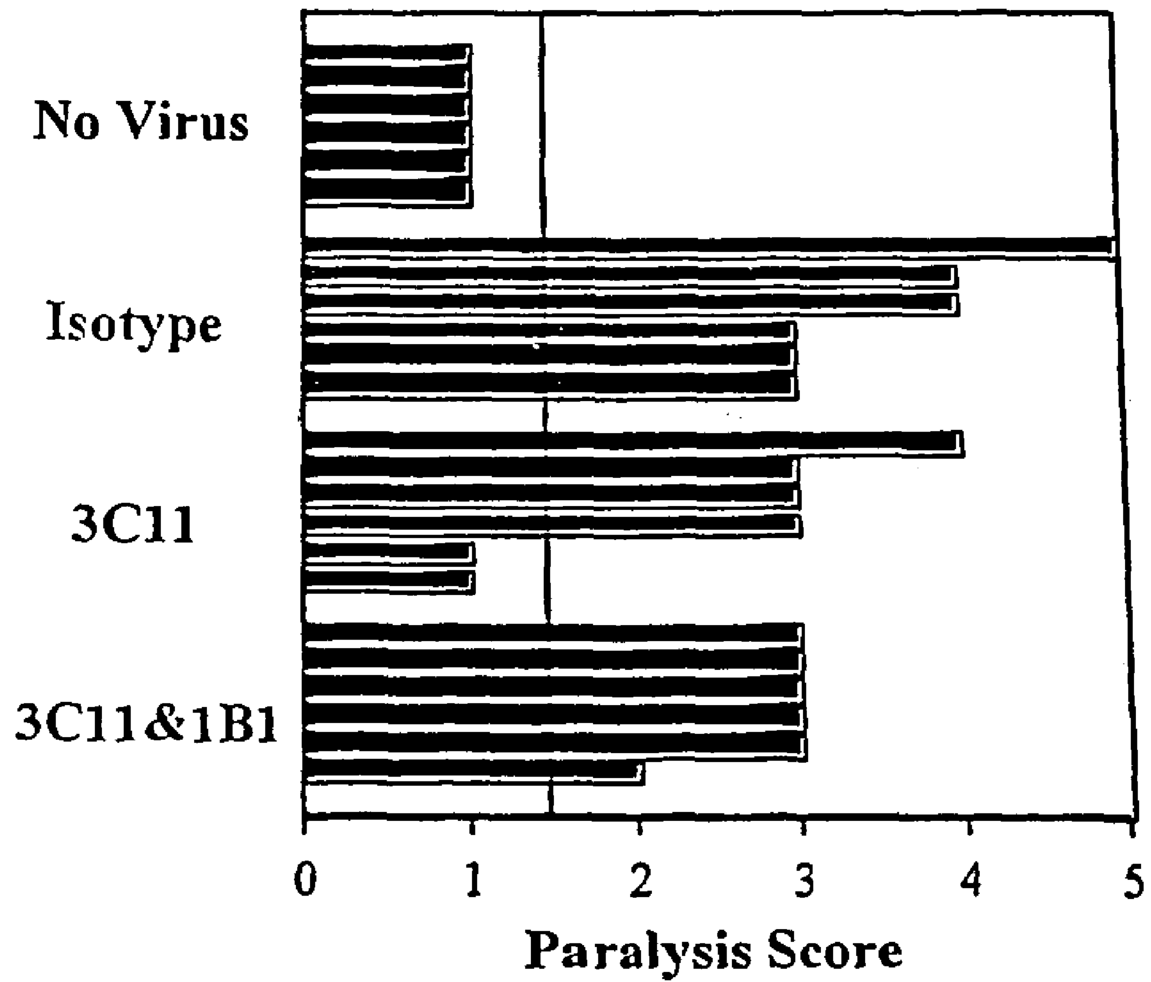
FIG. 3 is a graph showing protection against viral infection with an anti-CD1 monoclonal antibody. In the same experiment as shown in FIG. 2, mice were infected with EMCV-D and followed as described (Exley et al., Journal of Leukocyte Biology 69:713-718, 2001). Fifty mg of 3C11 anti-CD1 monoclonal antibody, 3C11 and 1B1 (from PharmEngine) anti-CD1 monoclonal antibodies, or isotype control monoclonal antibodies were given one day prior to infection. A paralysis score of one represents no paralysis. Mice with paralysis scores greater than the level represented by the vertical line in the figure were characterized as having viral infection-induced paralysis. The anti-CD1 antibodies significantly reduced paralysis in wild-type mice.
Figure 4:
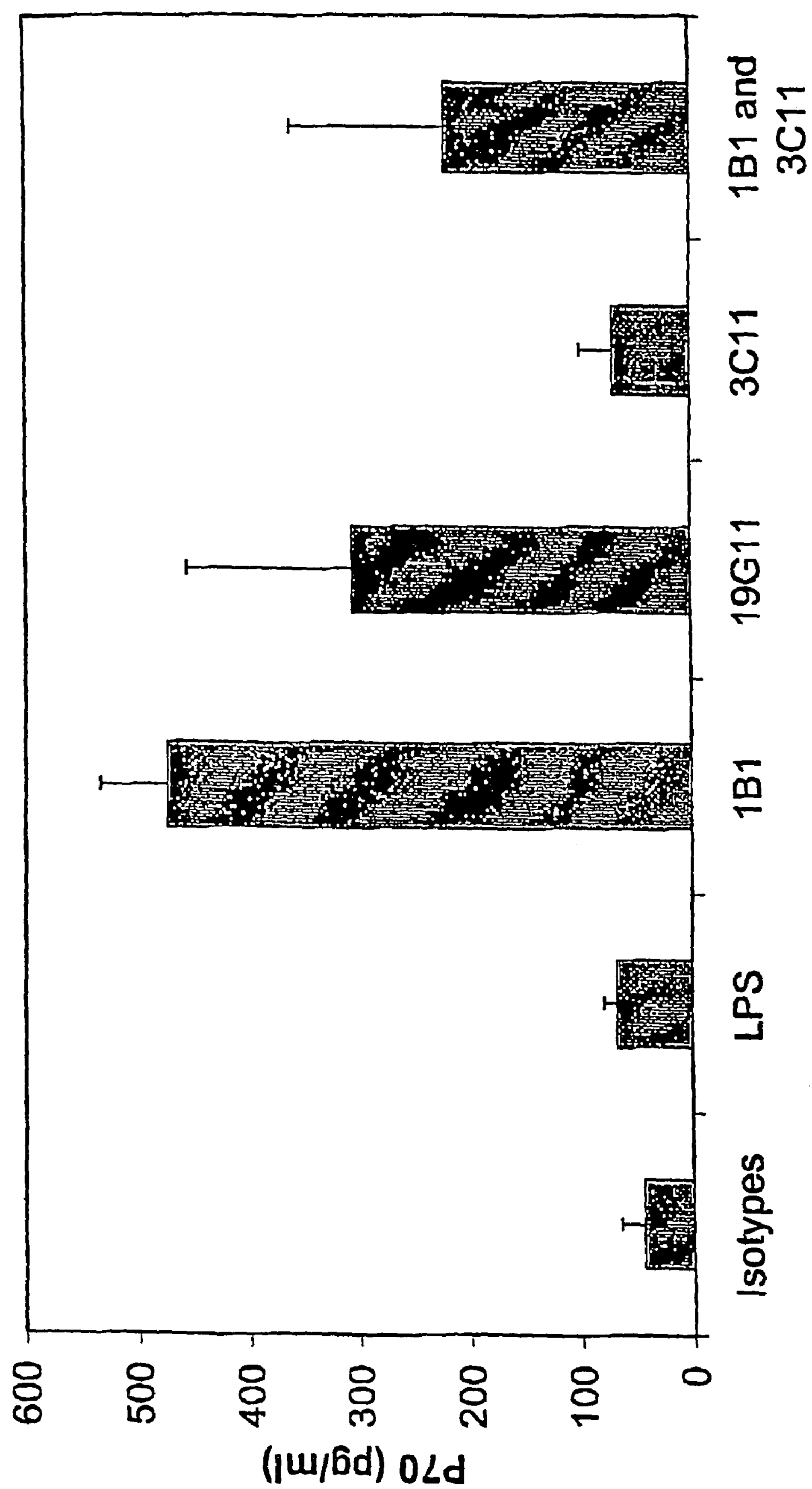
FIG. 4 is a graph showing the amount of IL-12 p70 released from isolated mouse spleen cells in the presence of IFNγ (150 pg/ml) (n=5). Mouse anti-CD1 antibodies (1B1, 19G11 and 3C11) were used to determine whether mouse CD1d positive cells release IL-12 p70 upon activation of CD1d. These results indicate that 1B1 and 19G11 antibodies activate CD1d positive cells to release IL-12 p70 in the presence of IFNγ. In the absence of IFNγ, there were no detectable IL-12 p70 in the supernatants.
Figure 5:
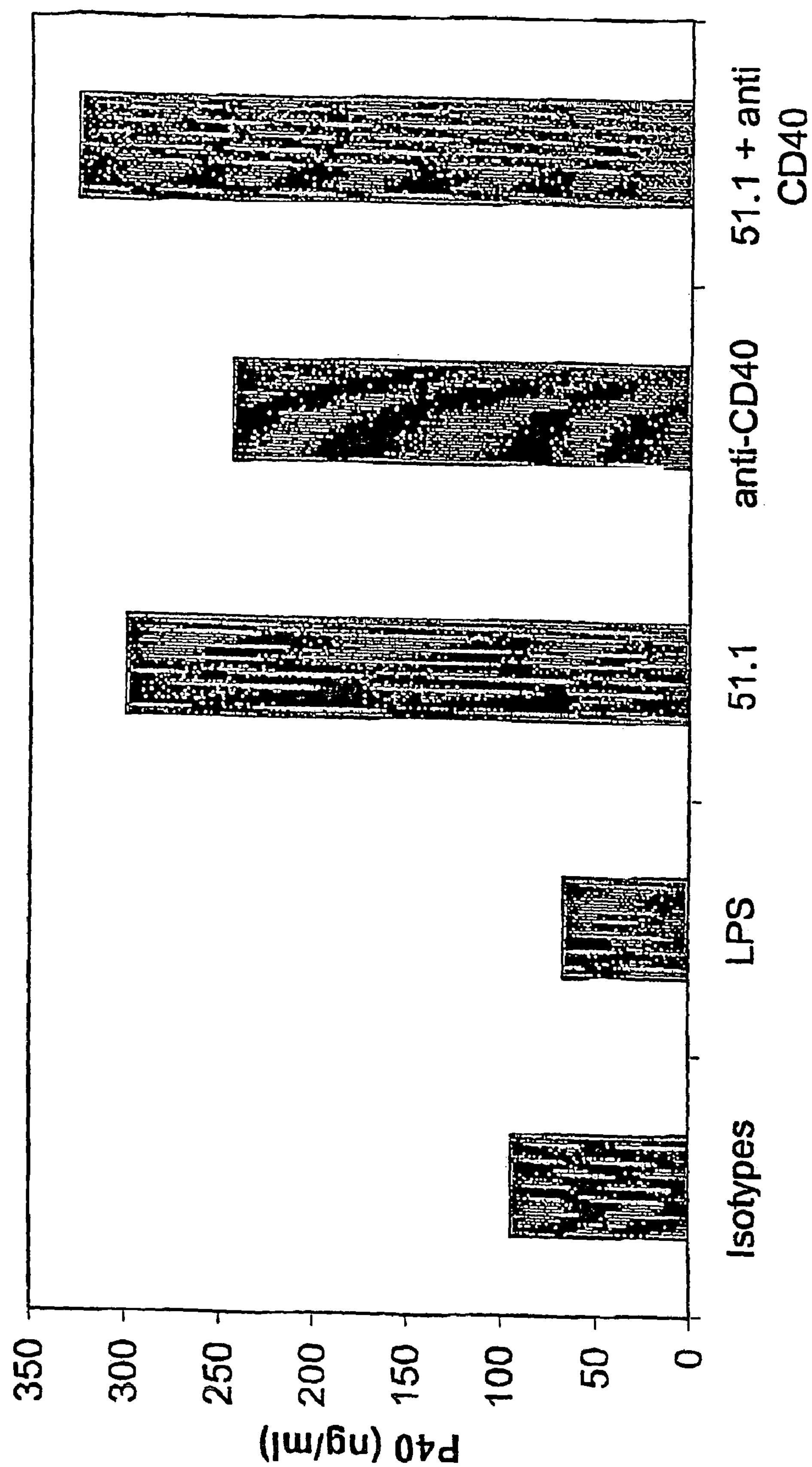
FIG. 5 is a graph showing the amount of IL-12 p40 released from adhered PBMC in the presence of IL-4 after 3 days (n=5). The experiment was stopped on the third day, and the supernatants were collected for IL-12 p40 measurements. IL-4 has been shown to enhance CD40 induced IL-12 p40 release from antigen presenting cells (APC). Adhered PBMC stimulated on 51.1 bounded plates released IL-12 p40 in the presence of IL-4 (10 ng/ml). This figure shows that IL-4 may enhance the release of IL-12 p40 from CD1d stimulated PBMC.
Figure 6:
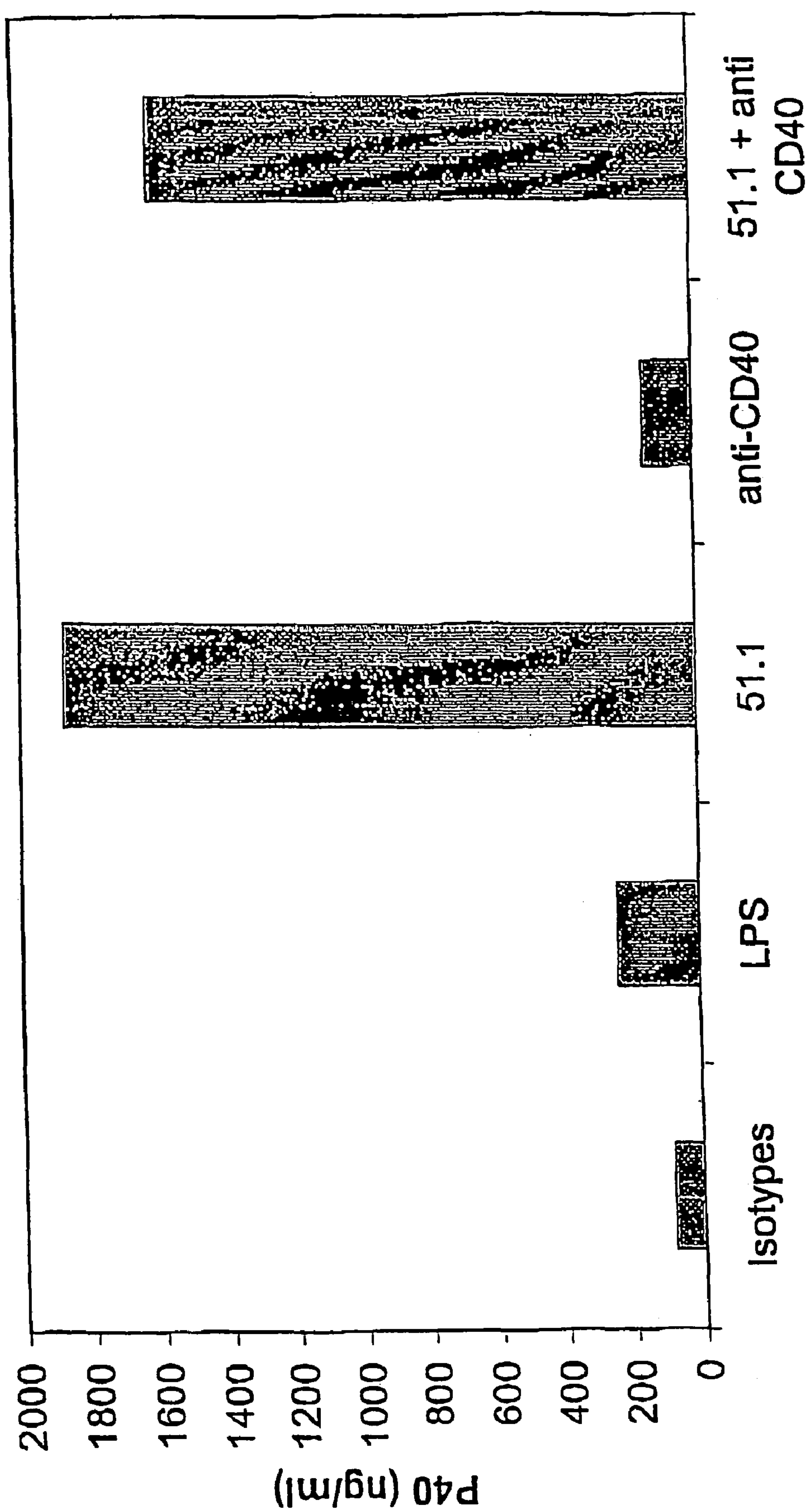
FIG. 6 is a graph showing the amount of IL-12 p40 released from adhered PBMC in the presence of IFNγ (20 ng/ml) after 3 days (n=5). The experiment was stopped on the third day, and the supernatants were collected for IL-12 p40 measurements. IFNγ has been shown to enhance CD40 induce IL-12 p40 release from APC. The increase in the amount of released of IL-12 p40 is much greater in the presence of IFNγ than in the presence of IL-4. Adhered PBMC stimulated on 51.1 bounded plates released IL-12 p40 in the presence of IFNγ (20 ng/ml). This figure shows that IFNγ may also enhance the release of IL-12 p40 from CD1d stimulated PBMC.
Figure 7:
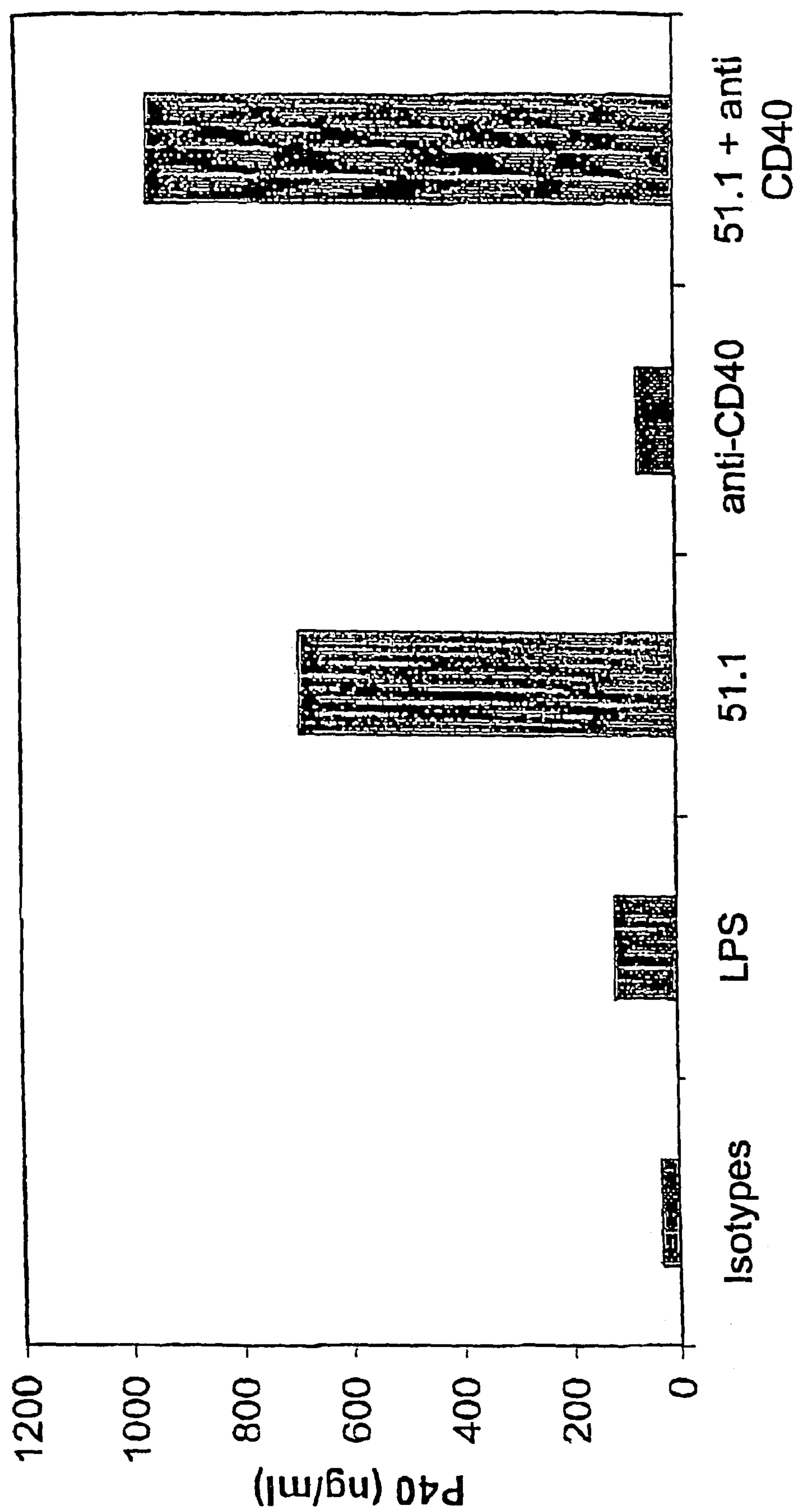
FIG. 7 is a graph showing the amount of IL-12 p40 released from adhered PBMC after three days (n=5). The experiment was stopped on the third day, and the supernatants were collected for IL-12 p40 measurements. Adhered PBMC stimulated on 51.1 bounded plates released IL-12 p40. The release of IL-12 p40 was less than the release of IL-12 p40 in the experiments carried out in the presence of IFNγ but greater than the release of IL-12 p40 in the presence of IL-4. This figure also demonstrates that IFNγ enhances the release of IL-12 p40 from adhered PBMC that is induced by an anti-CD1d antibody.
Figure 8:
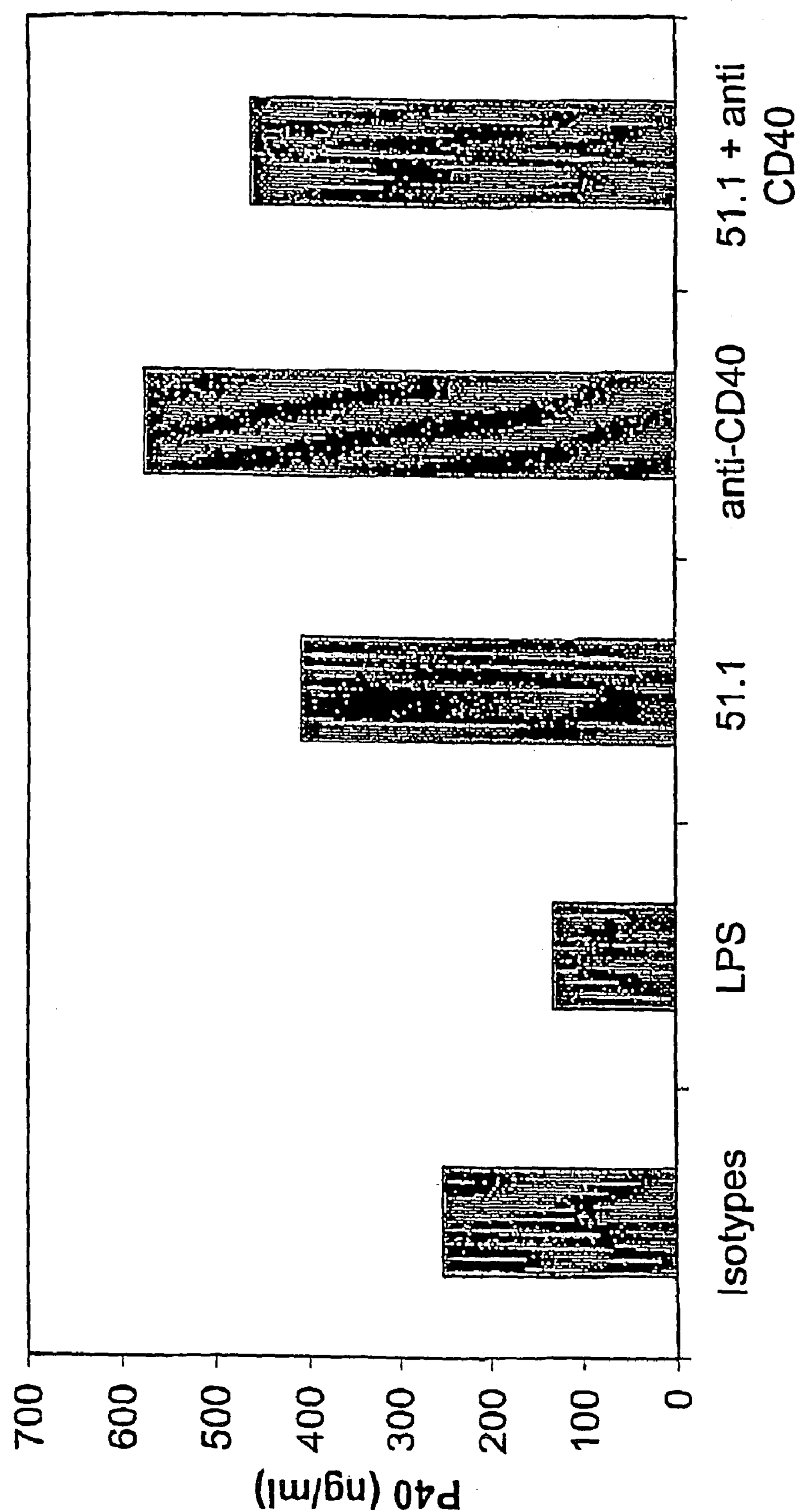
FIG. 8 is a graph showing the amount of IL-12 P40 released from adhered PBMC in the presence of IL-4 (10 ng/ml) and IFNγ (20 ng/ml) after three days (n=5). The experiment was stopped on the third day, and the supernatants were collected for IL-12 p40 measurements. Adhered PBMC stimulated on 51.1 bounded plates released IL-12 p40. The release of IL-12 p40 was less than the release of IL-12 p40 in the experiments carried out in the presence of IFNγ. This figure suggests that IFNγ may enhance the anti-CD1d antibody induced release of IL-12 p40 more than a combination of IFNγ and IL-4.
Figure 9:
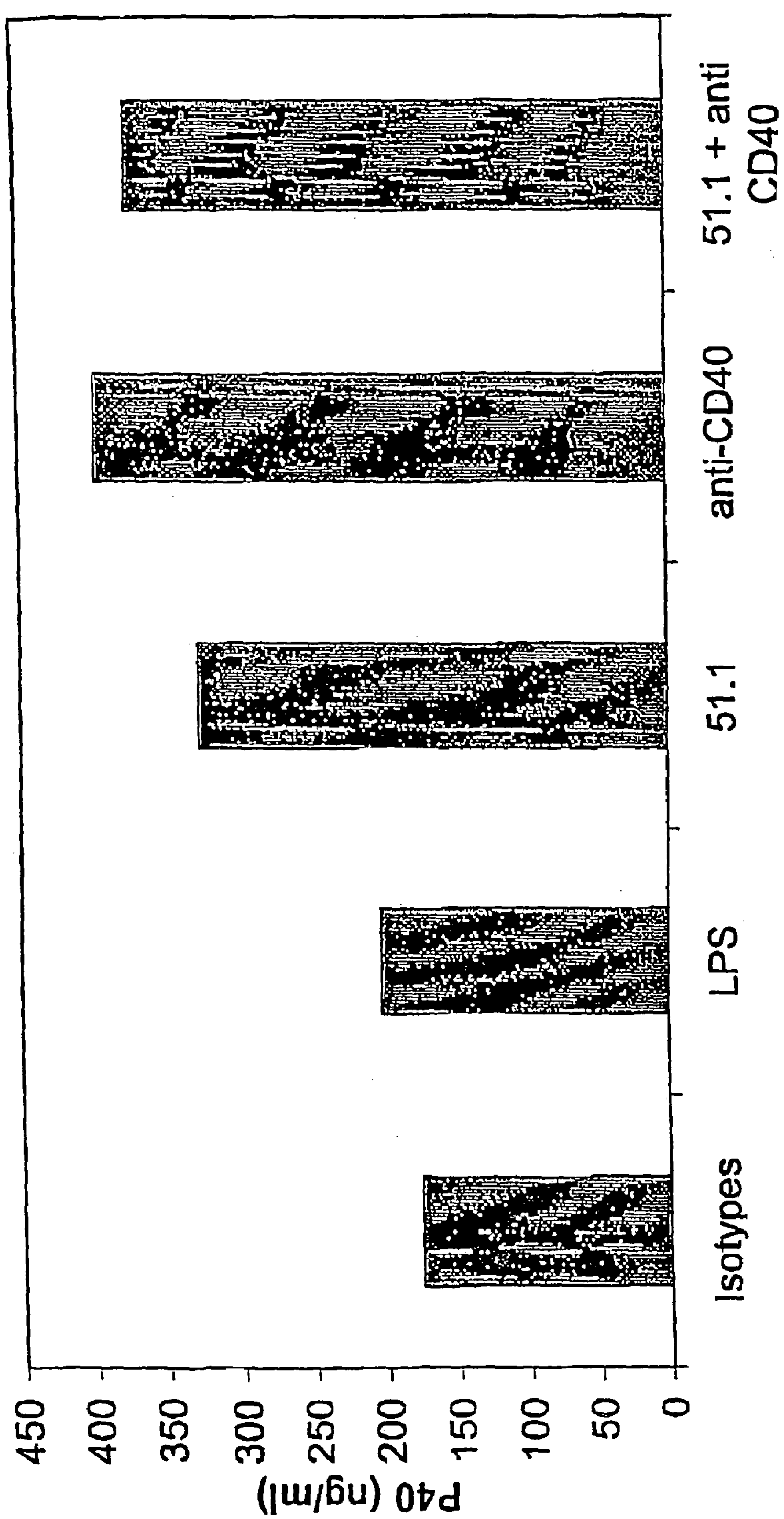
FIG. 9 is a graph showing the amount of IL-12 p40 released from adhered PBMC, in the presence of IL-4 (10 ng/ml) after 8 days (n=5). The experiment was stopped on the eighth day, and the supernatants were collected for IL-12 p40 measurements. Adhered PBMC stimulated on 51.1 bounded plates released IL-12 p40 in the presence of IL-4 (10 ng/ml). This figure shows that IL-4 is may enhance the release of IL-12 p40 from CD1d stimulated PBMC.
Figure 10:
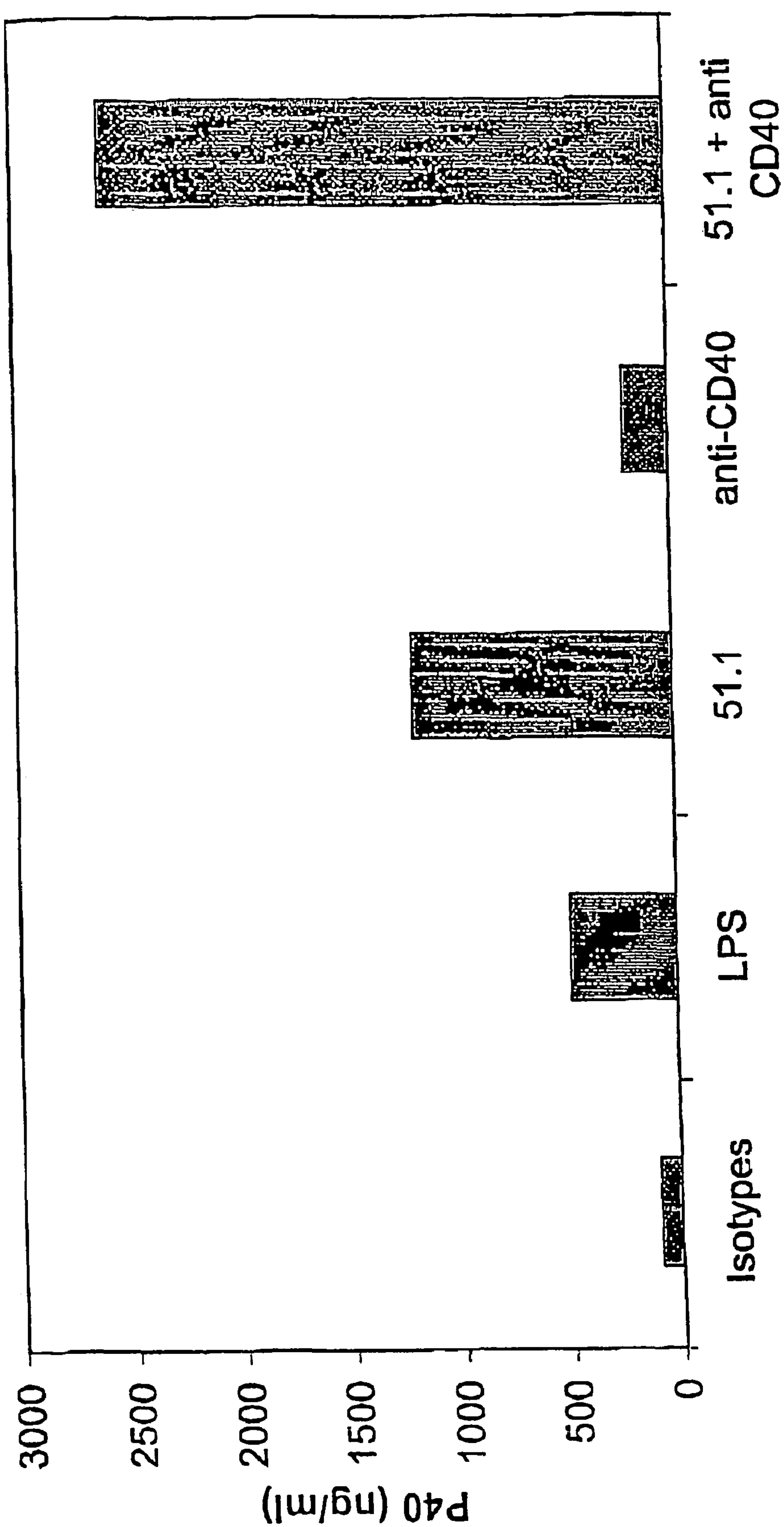
FIG. 10 is a graph showing the amount of IL-12 p40 released from adhered PBMC in the presence of IFNγ (20 ng/ml) after eight days (n=5). The experiment was stopped on the eighth day, and the supernatants were collected for IL-12 p40 measurements. IFNγ has been shown to enhance CD1d induce IL-12 p40 released from APC as shown above. Adhered PBMC stimulated on 51.1 bounded plates released IL-12 p40 in the presence of IFNγ (20 ng/ml). The increase of IL-12 p40 was much greater in the presence of IFNγ than in the presence of IL-4. This figure shows that IFNγ may enhance the release of IL-12 p40 release from CD1d stimulated PBMC. The amount of released IL-12 p40 was similar to the amount released at an earlier time point (3 day).
Figure 11:
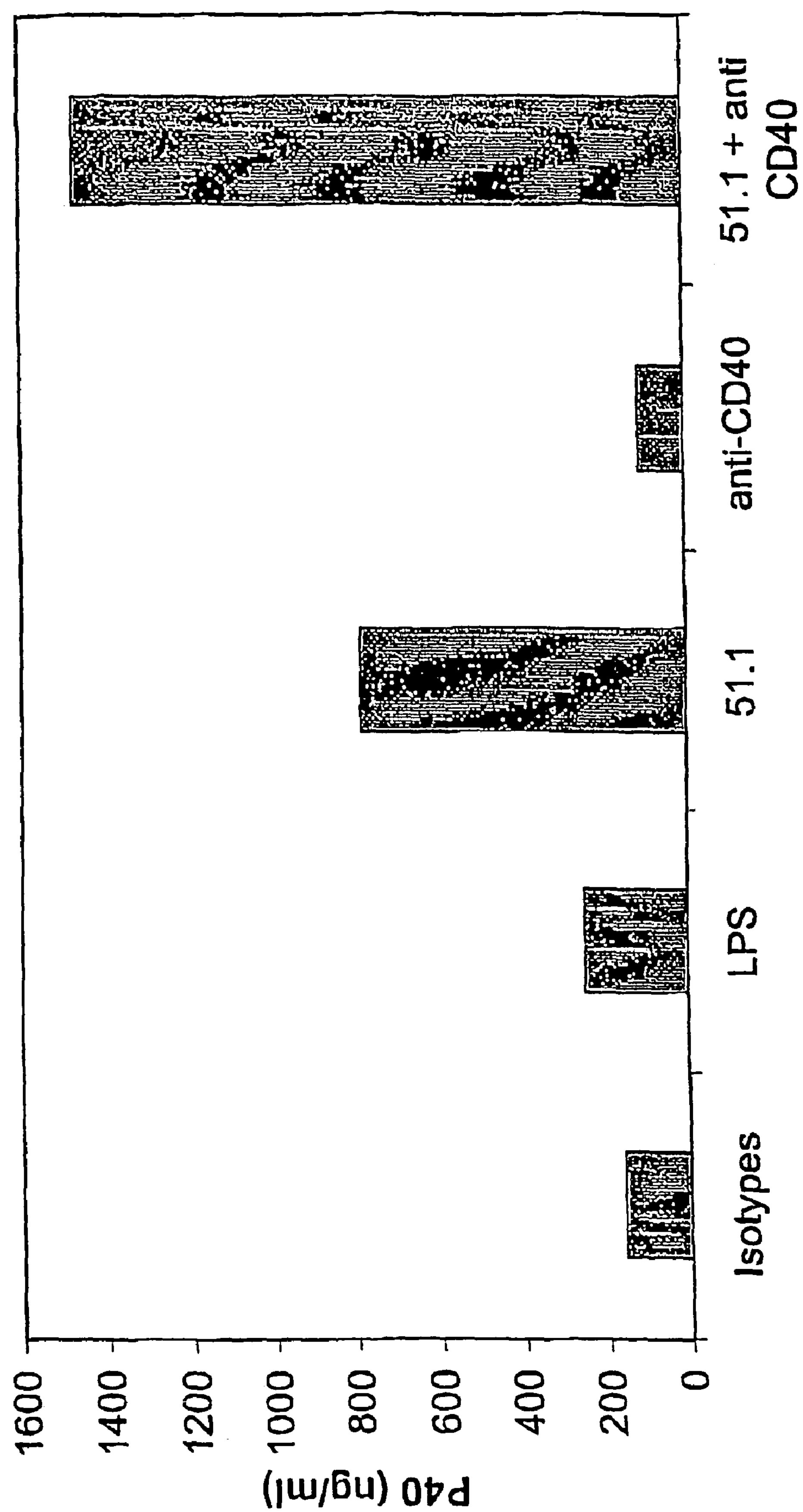
FIG. 11 is a graph showing the amount of IL-12 p40 released from adhered PBMC after eight days (n=5). The experiment was stopped on the eighth day, and the supernatants were collected for IL-12 p40 measurements. Adhered PBMC stimulated on 51.1 bounded plates released IL-12 p40. The release of IL-12 p40 was less than the amount released in the presence of IFNγ (FIG. 10) but greater than the amount released in the presence of IL-4 (FIG. 9). This figure shows also that IFNγ enhances the release of IL-12 p40 release from CD1d stimulated PBMC.
Figure 12:
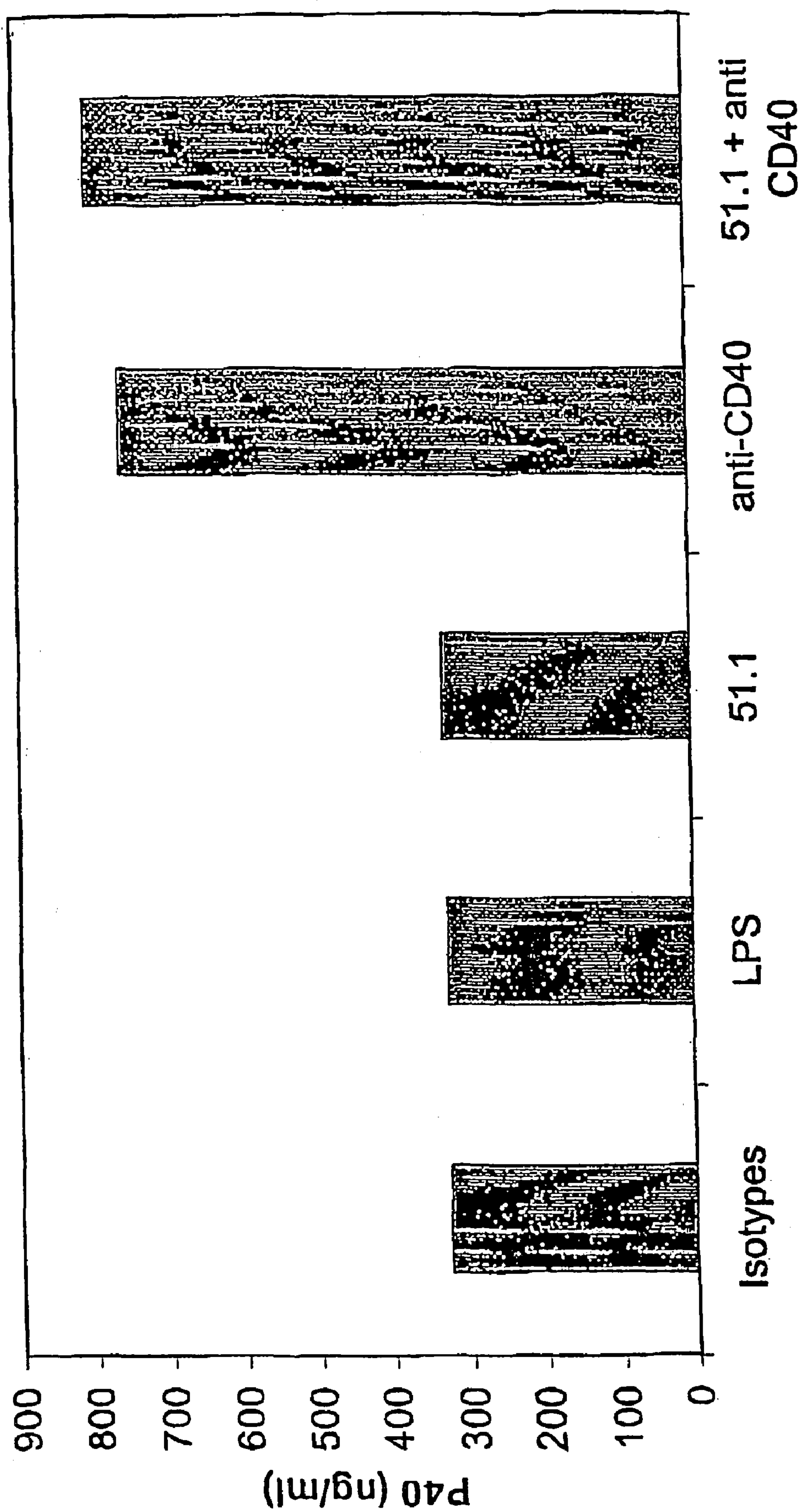
FIG. 12 is a graph showing the amount of IL-12 p40 released from adhered PBMC in the presence of IL-4 (10 ng/ml) and IFNγ (20 ng/ml) after eight days (n=5). The combination of cytokines IL-4 and IFNγ did not induce the release of IL-12 p40. Later experiments were all carried out using the early time points and with IFNγ since this condition results in a larger measurable production of IL-12 p40 from PBMC.
Figure 13:
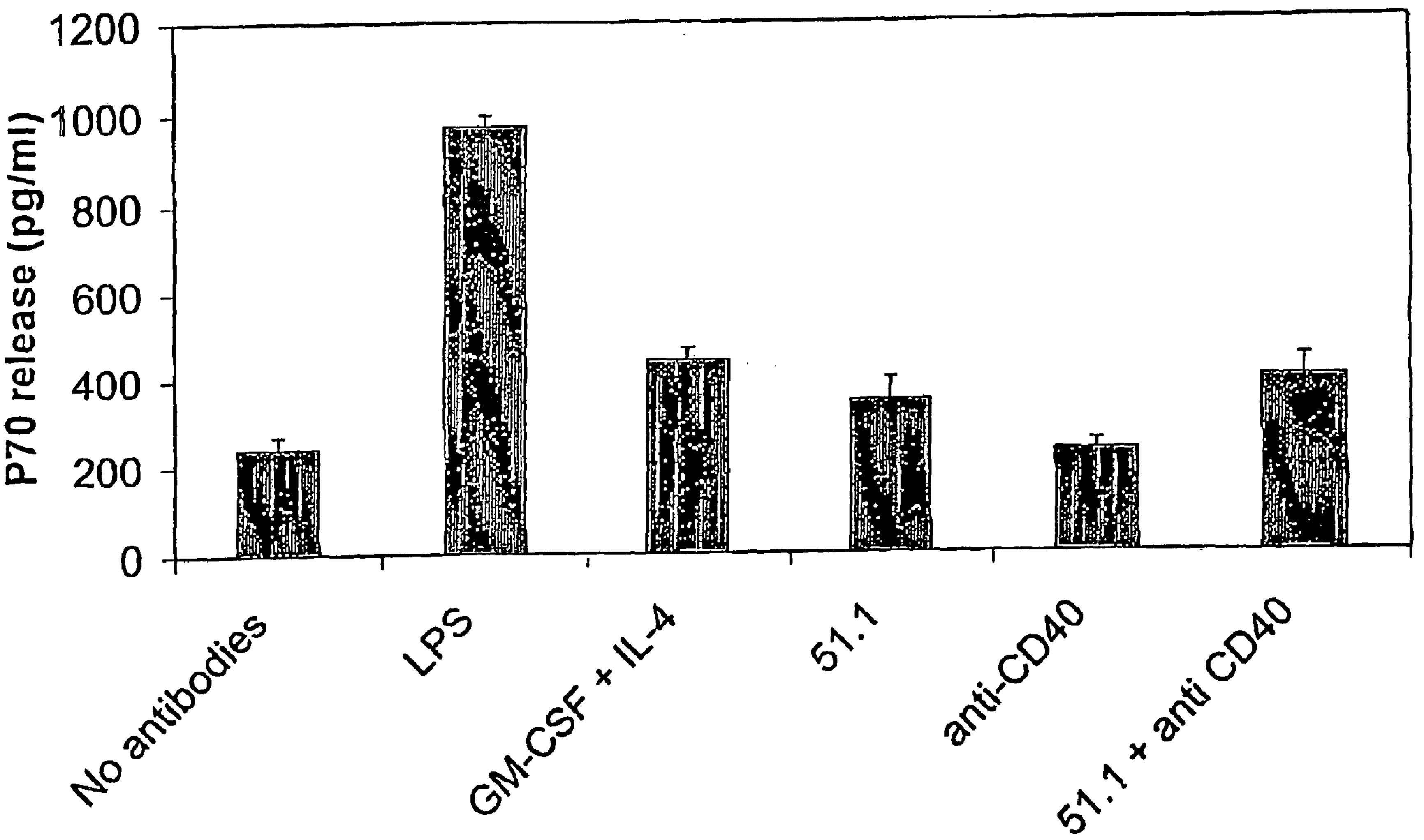
FIG. 13 is a graph showing the amount of IL-12 p70 released from C1Rd in the presence of PMA (2.5 ng/ml) after two days (n=5). C1Rd cells were unable to release IL-12 p70 upon CD40 or CD1d stimulation under the conditions tested.
Figure 14:
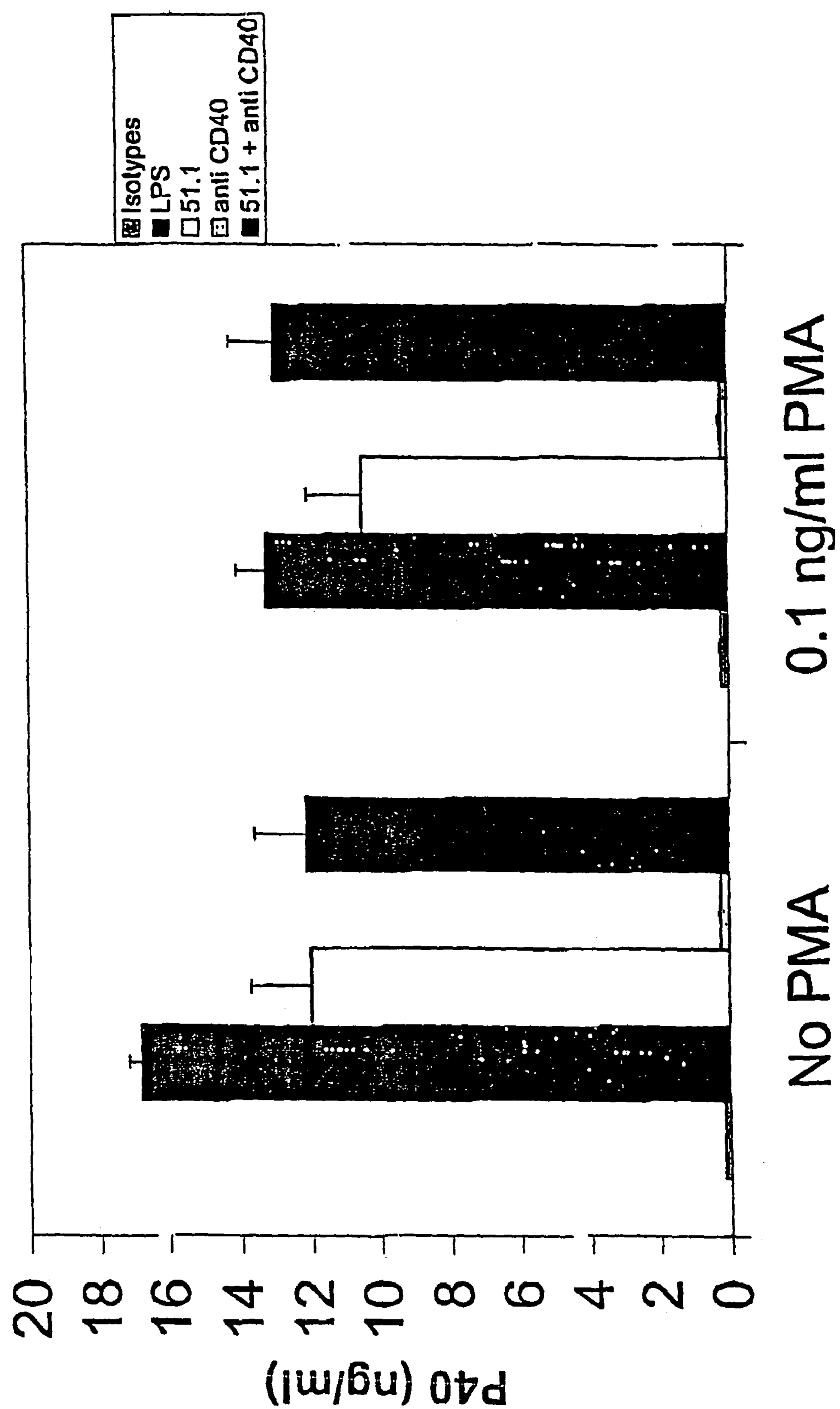
FIG. 14 is a graph showing the amount of IL-12 p40 released from THP-1 cell with and without PMA (0.1 ng/ml), 2% serum media, and IFNγ (20 ng/ml) after two days (n=5). There were no significant differences in the experiments carried out with or without PMA.
Figure 15:
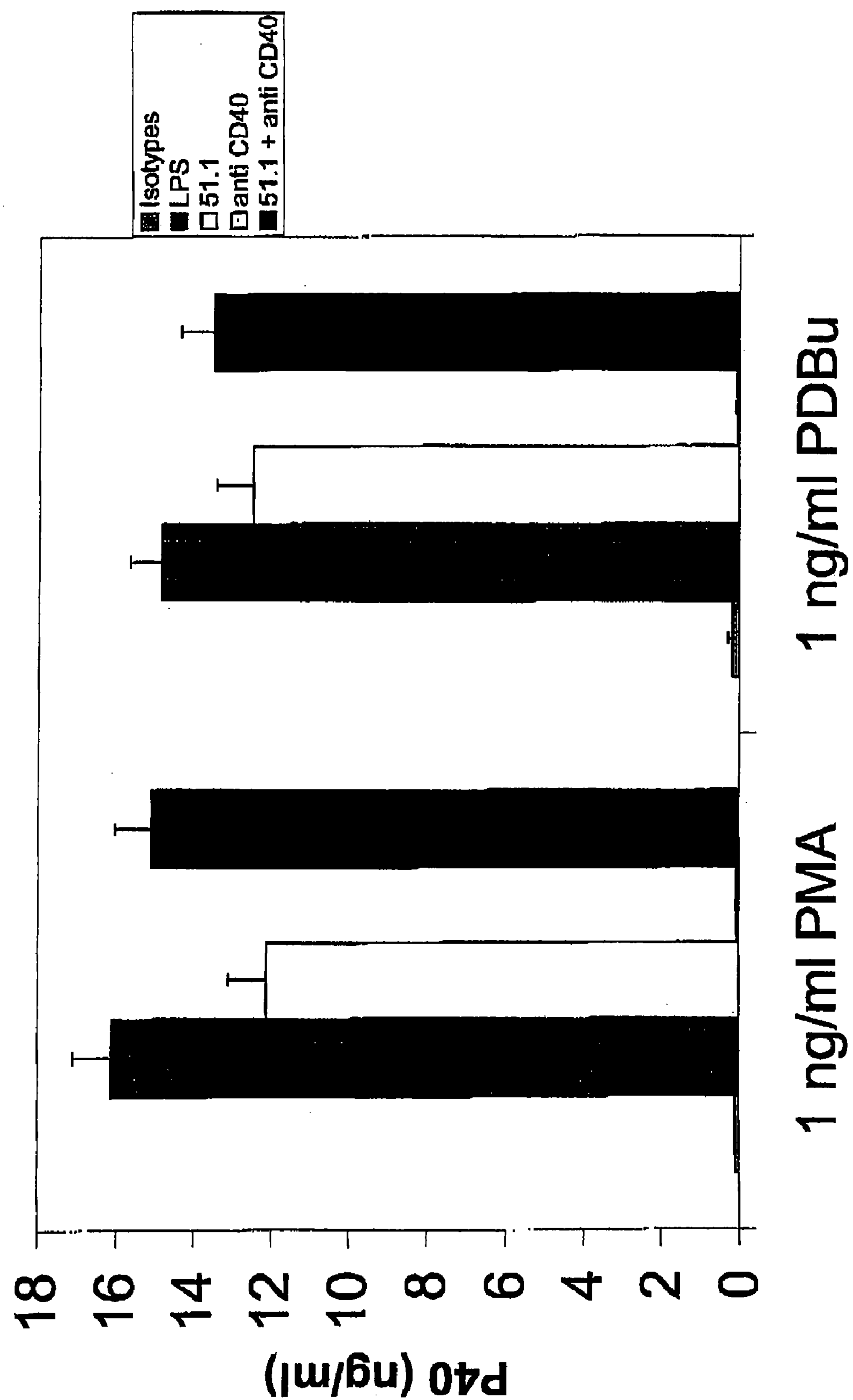
FIG. 15 is a graph showing the amount of IL-12 p40 released from THP-1 cell with PMA/PDBu (1 ng/ml), 2% serum media, and IFNγ (20 ng/ml) after two days (n=5). There were no significant differences in the experiments carried out with or without PMA/PDBu.
Figure 16:
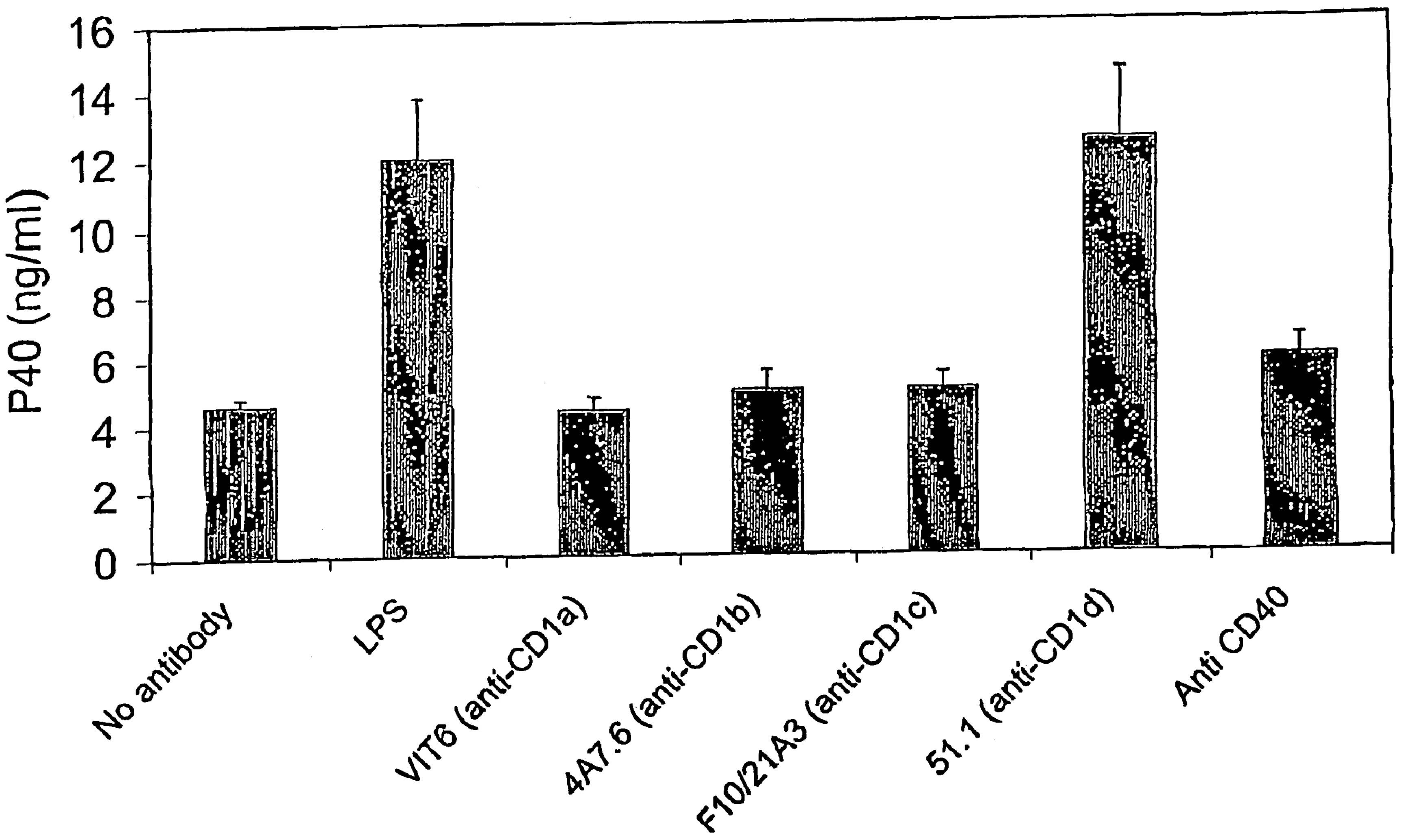
FIG. 16 is a graph showing the amount of IL-12 p40 released from THP-1 induced by different antibodies in the presence of IFNγ (20 ng/ml) on day 1 (n=5). A variety of anti-CD1 antibodies (VIT6, 4A7.6, F10/21A3 and 51.1) and an anti-CD40 antibody were used. After one day, the only antibody that was able to stimulate the cells to produce IL-12 p40 was 51.1. The amount of IL-12 p40 released was comparable to the amount released from cells stimulated with LPS.
Figure 17:
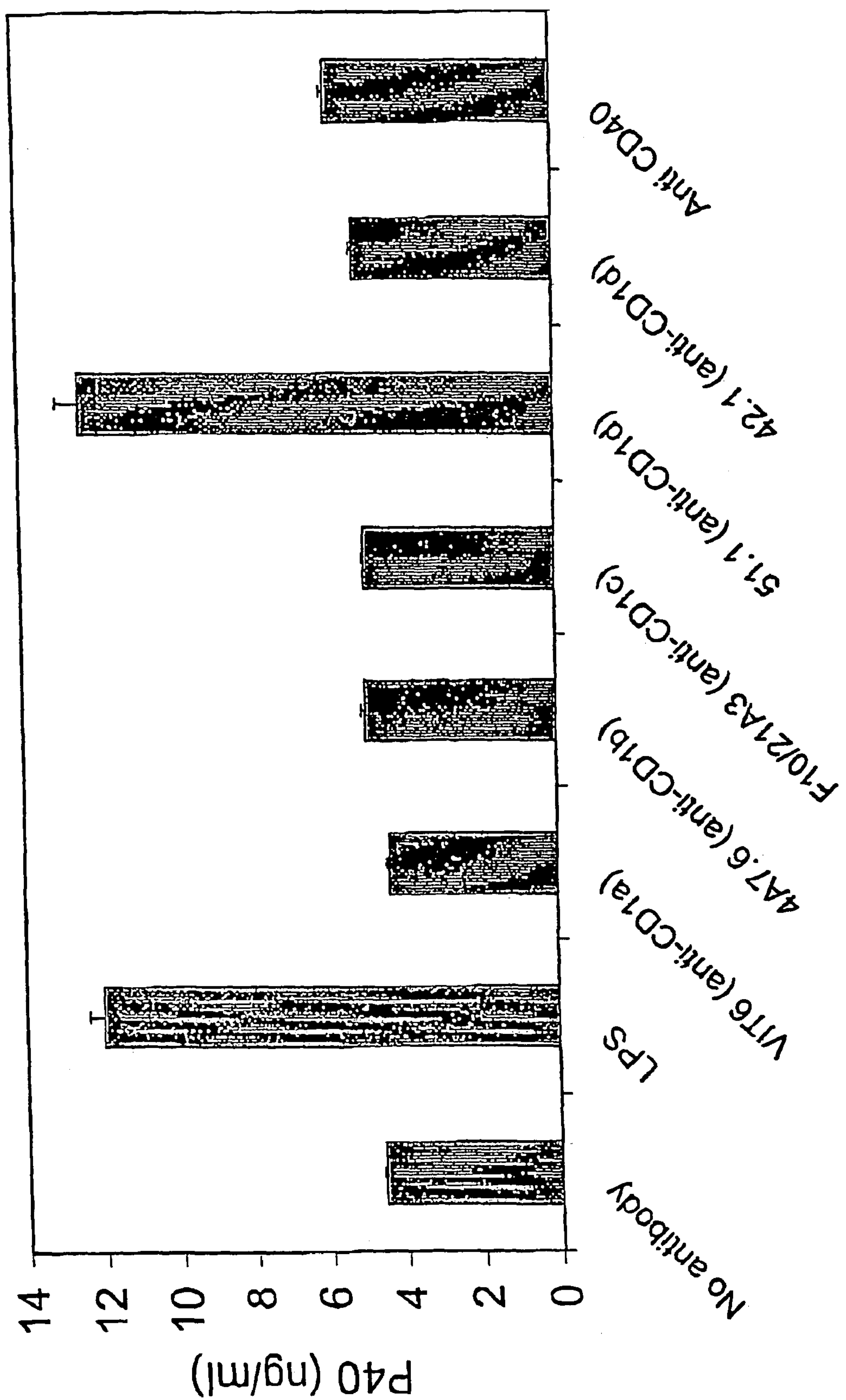
FIG. 17 is a graph showing the amount of IL-12 p40 released from THP-1 induced by different antibodies in the presence of IFNγ (20 ng/ml) after three days (n=5). A variety of anti-CD1 antibodies (VIT6, 4A7.6, F10/21A3 and 51.1) and an anti-CD40 antibody were used. After 2 more days the only antibody that was able to stimulate the cells to produce IL-12 p40 was 51.1. The amount of IL-12 p40 seen was comparable to cells which were stimulated with LPS.
Figure 18:
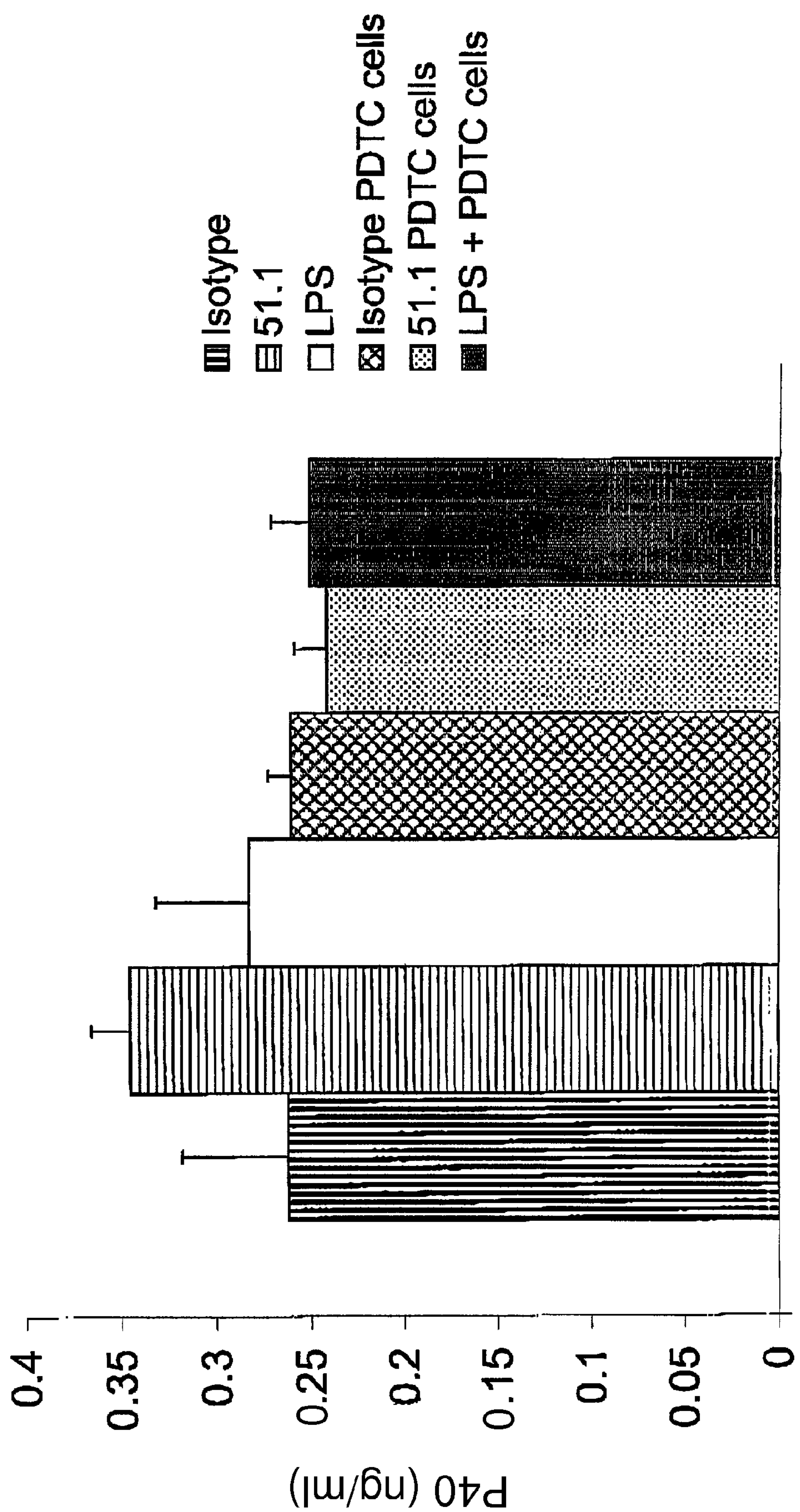
FIG. 18 is a graph showing the amount of IL-12 p40 released from THP-1 using all soluble antibodies and serum free media without IFNγ after two days (n=5). Cross-linking of soluble antibodies using anti-mouse IgG did not induce IL-12 p40 release from THP-1 cells but inhibited the release of IL-12 p40 from all cells tested, including the positive control (LPS). These results suggest that an anti-CD1 antibody bound to a plate may stimulate IL-12 production more than the corresponding soluble anti-CD1 antibody.
Figure 19:
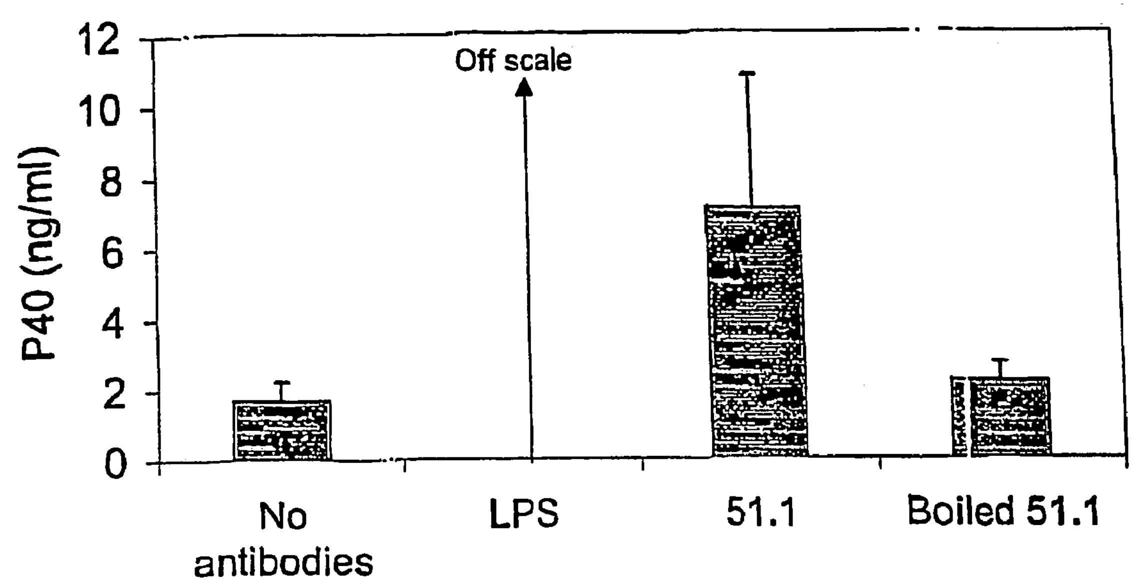
FIG. 19 is a graph demonstrating that the induction of IL-12 p40 release by the 51.1 antibody was not due to endotoxins (n=5). The 51.1 antibody was heated at 100° C. for 30 minutes to destroy the antibody structure to determine whether cell activation was solely due to the antibody and not due to endotoxins. After two days, the amount of released IL-12 p40 was measured. The results demonstrate that the boiled antibody was unable to stimulate the cells, and thus, the release of IL-12 p40 was solely due to CD1d activation.
Figure 20:
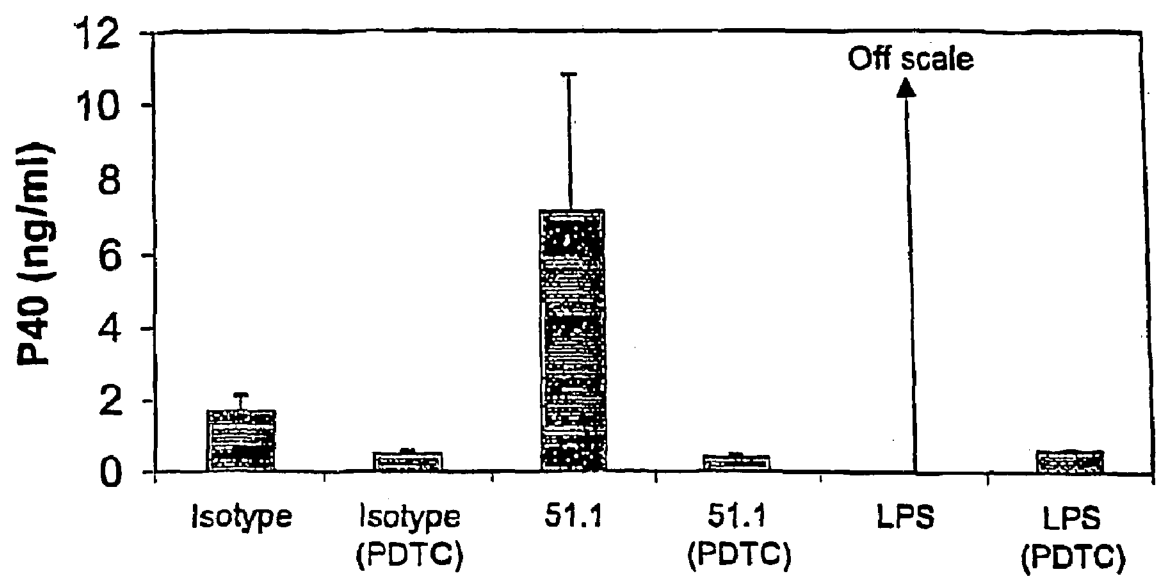
FIG. 20 is a graph demonstrating the effect of an NFκB inhibitor (PDTC) on the release of IL-12 p40 induced by the 51.1 anti-CD1 antibody and LPS (n=5). This figure shows that NFκB is involved in the transcription of IL-12 p40.
Figure 21:
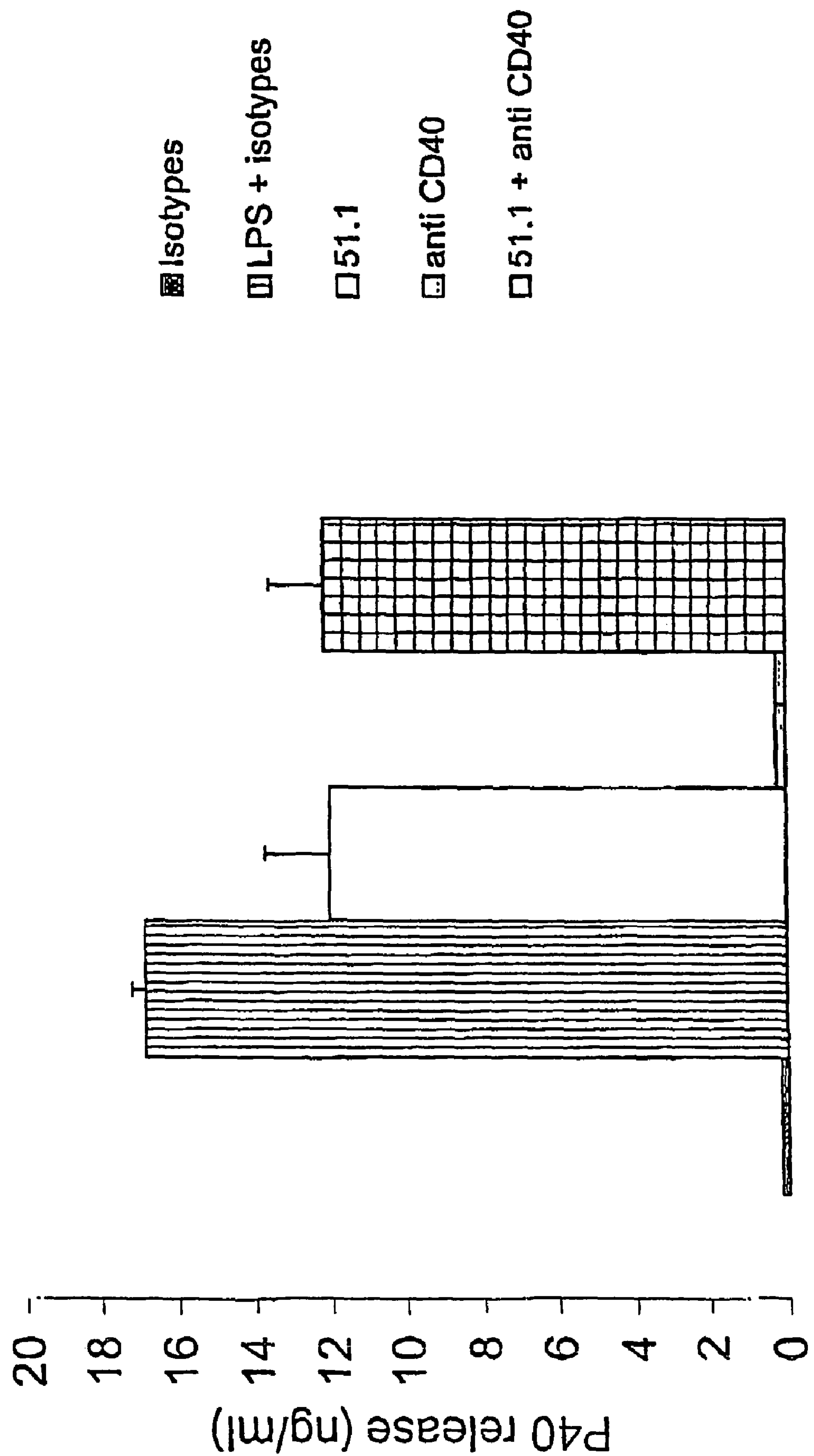
FIG. 21 is a graph showing the amount of IL-12 p40 released from THP-1 cells in the presence of IFNγ (10 ng/ml) and 2% serum media after two days (n=5).
Figure 22:
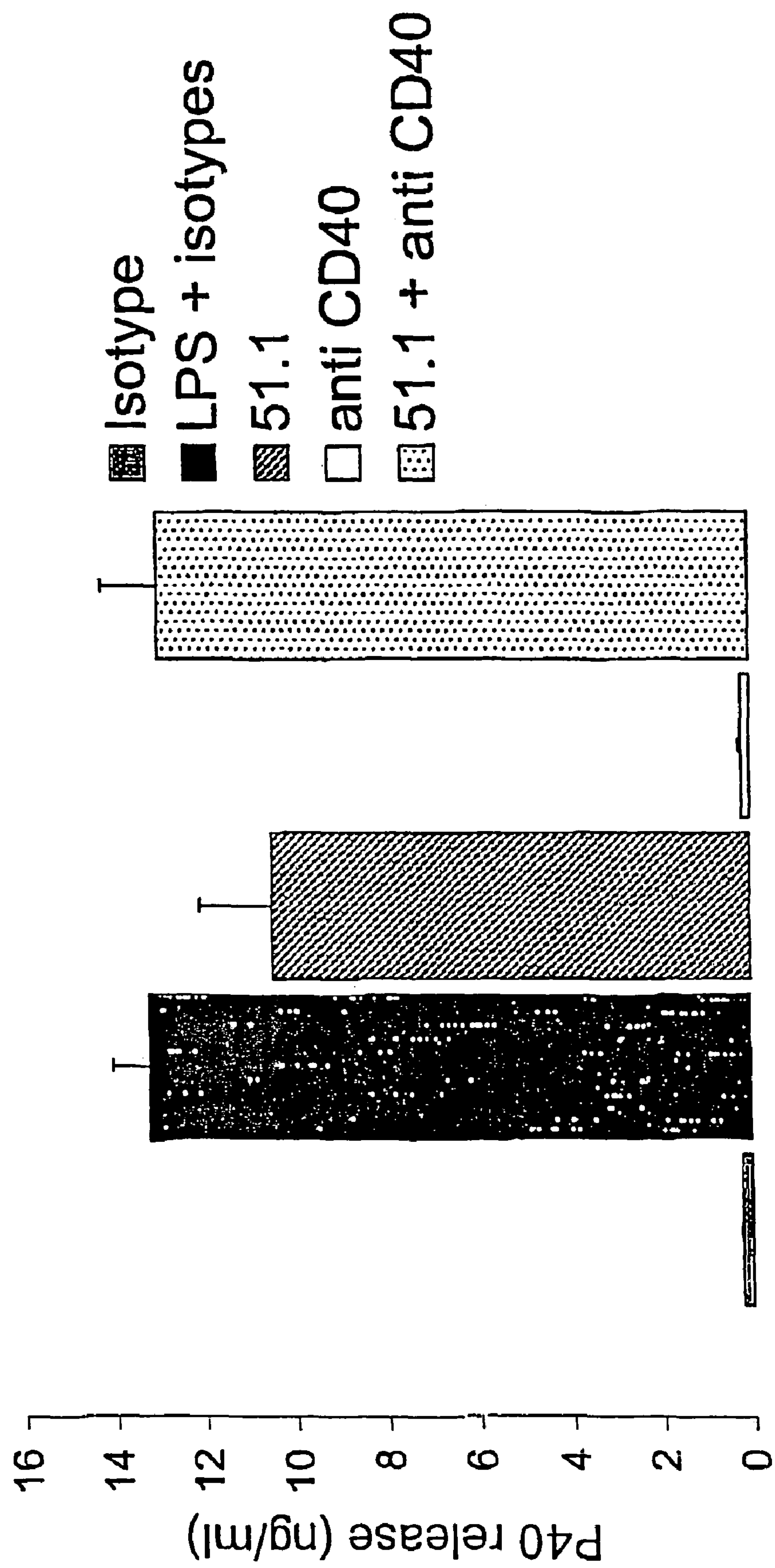
FIG. 22 is a graph showing the amount of IL-12 p40 released from THP-1 cells IFNγ (10 ng/ml) and 2% serum media (1 ng/ml PMA) after two days (n=5).

As illustrated in FIG. 1, administration of the anti-CD1 monoclonal antibody 3C11 prevented diabetes in wild-type mice infected with EMCV-D. In contrast, 33% of the wild-type mice that were administered a control antibody prior to EMCV-D infection became diabetic. These results were confirmed in an independent experiment. Additionally, the administration of both 3C11 and 1B1 anti-CD1 monoclonal antibodies further reduced glucose levels in viral infected mice (FIG. 2). The administration of 3C11 antibody or 1B1 and CD1 antibodies also reduced the severity of paralysis induced by EMCV-D infection (FIG. 3).

FIG. 1 also demonstrates that CD1 knockout mice have a much higher incidence of diabetes (100%) compared to uninfected, wild-type mice (0%). This result supports the important role of CD1-expressing cells in the prevention of undesired immune responses, such as viral infection-induced diabetes.

EXAMPLE 3

Ability of Anti-CD1 Antibodies to Enhance Production of Cytokines by Murine and Human Antigen Presenting Cells IL-12 is an inducible cytokine composed of 35 kDa and 40 kDa subunits that are critical in inducing helper type 1 T cells during initial immune responses to pathogens. The 40 kDa subunit, expressed by activated antigen presenting cells, is induced by pathogens. Control of IL-12 p40 expression is therefore important for understanding resistance and susceptibility to pathogens.

To demonstrate the ability of anti-CD1 antibodies to increase the production of IL-12, mouse CD1d positive splenocyte cells, human peripheral blood mononuclear cells (PBMC), and human THP-1 monocytic cell line were analyzed. PBMC were obtained from healthy adult volunteers of both sexes on Ficoll Hypaque density gradients and cultured in complete medium consisting of RPMI 1640 and 10% FBS. THP-1 is a human monocytic leukaemia cell line. Compared to other human myeloid cell lines, such as HL-60 and U937, THP-1 cells express CD1d on their surfaces. Because of this characteristic, the THP-1 cell line provides a valuable model for studying the mechanism involved in CD1d crosslinking by measuring the IL-12 and phospho kinases in the cell. THP-1 cells was cultured in complete medium consisting of RPMI 1640 and 10% FBS.

For the activation of these target cells, an anti-CD1 antibody was bound to a plate and then incubated with the cells. In particular, 98-well plates were coated with 10 μg/ml protein G overnight at 4° C. Wells were washed with PBS and blocked with BSA at room temperature for four hours. Antibody (10 μg/ml) was added to each well for four hours at room temperature. The wells were washed again to remove the unbound antibodies, and $1.5\times10^5$ to $2\times10^5$ cells were added to each well in RPMI 1640 culture media.

Figure 23:
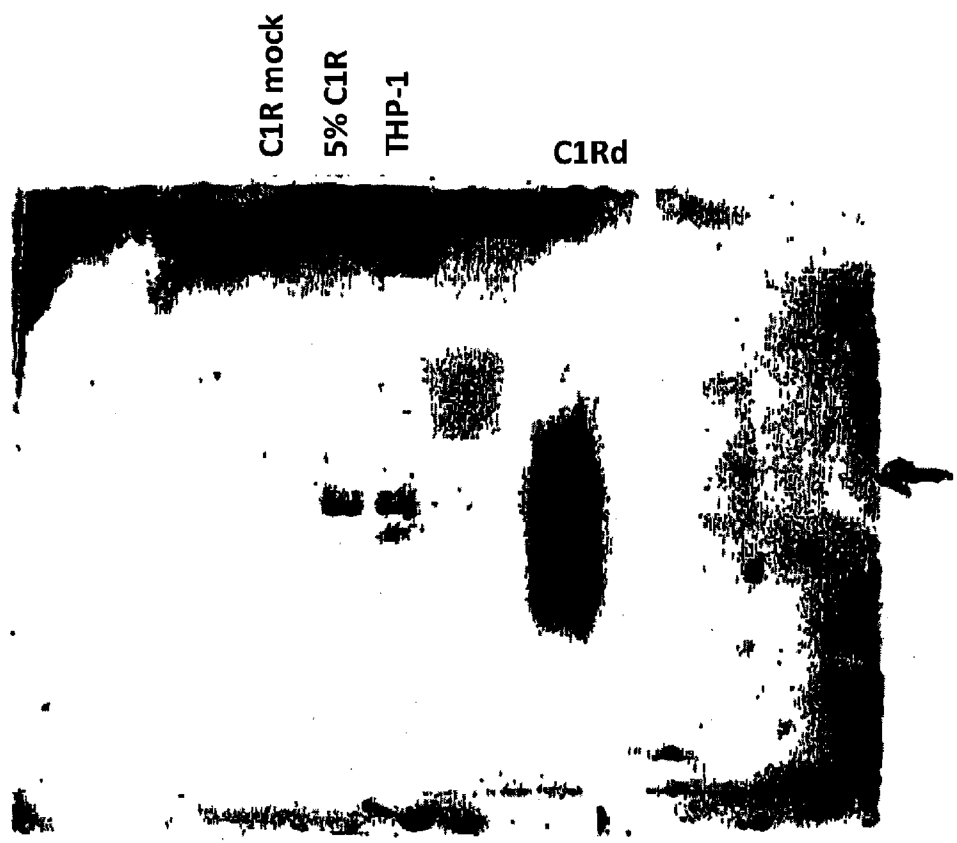
FIG. 23 is a picture of a Western blot showing the present of CD1d in THP-1 cells. The CD1d band shown on the blot indicates that THP-1 cells have CD1d either in the cells or expressed on the cell surface.
Figure 24:
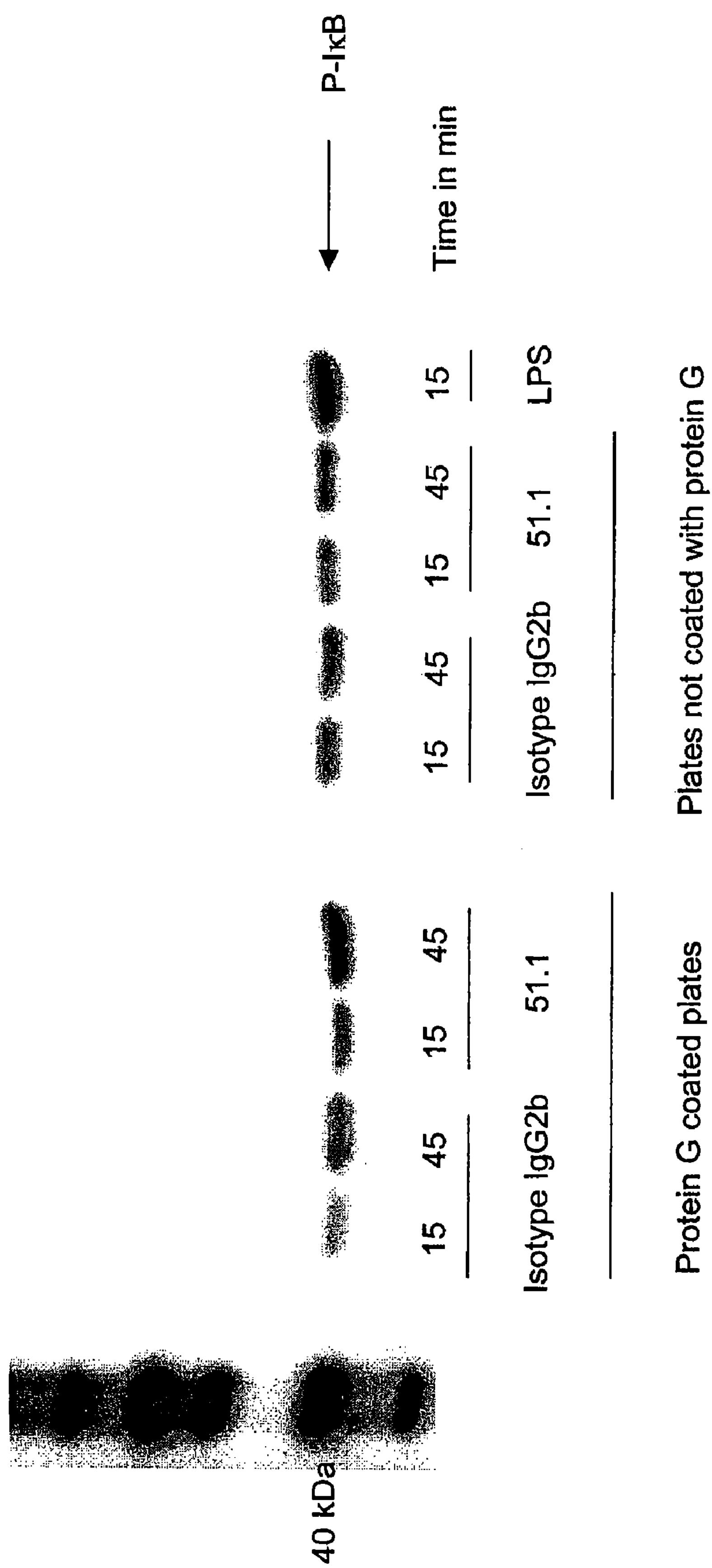
FIG. 24 is a picture of a Western blot showing the increased levels of P—IκB in THP-1 cells during stimulation with the 51.1 anti-CD1d antibody. No increase of P—IκB was observed on the western blot when the cells were put on plates that were not coated with protein G prior to 51.1. In contrast, plates that were coated with protein G prior to 51.1 were able to stimulate the cells. The level of p-IκB in cells after 45 minutes of 51.1 stimulation was similar to the levels found in LPS stimulated cells. These results indicate that cross-linking of CD1d with protein G is required for NFκB activation.

To confirm the presence of CD1d on the surface of THP-1 cells, fluorescent staining of cells were performed using the 51.1 monoclonal anti-CD1d antibody and fluorescently labeled anti-human IgG (H+L) HAS. Stained cells were analysed on a FACSCAN cytometer (FIGS. 26A-26D, 27A-27D, and 28A-28D). To measure the level of CD1d expressed by THP-1 cells or to measure the level of P-IκB induced by an anti-CD1 antibody, equal amounts of cytosolic extracts were separated on a 10% SDS-PAGE gel and transferred to a nitocellulose membrane (FIGS. 23 and 24). The membranes were blocked in 5% BSA in TBST, incubated with the primary antibody and detected with horseradish peroxidase-conjugated secondary antibody and enhanced chemilluminesence substrate.

To measure the increase induction of IL-12 production by an anti-CD1 antibody, the concentrations of P40 and P70 forms of IL-12 in cultured supernatants were measured with a standard sandwich ELISA technique using combinations of monoclonal antibodies to different epitopes of each cytokine (FIGS. 4-22).

Figure 29:
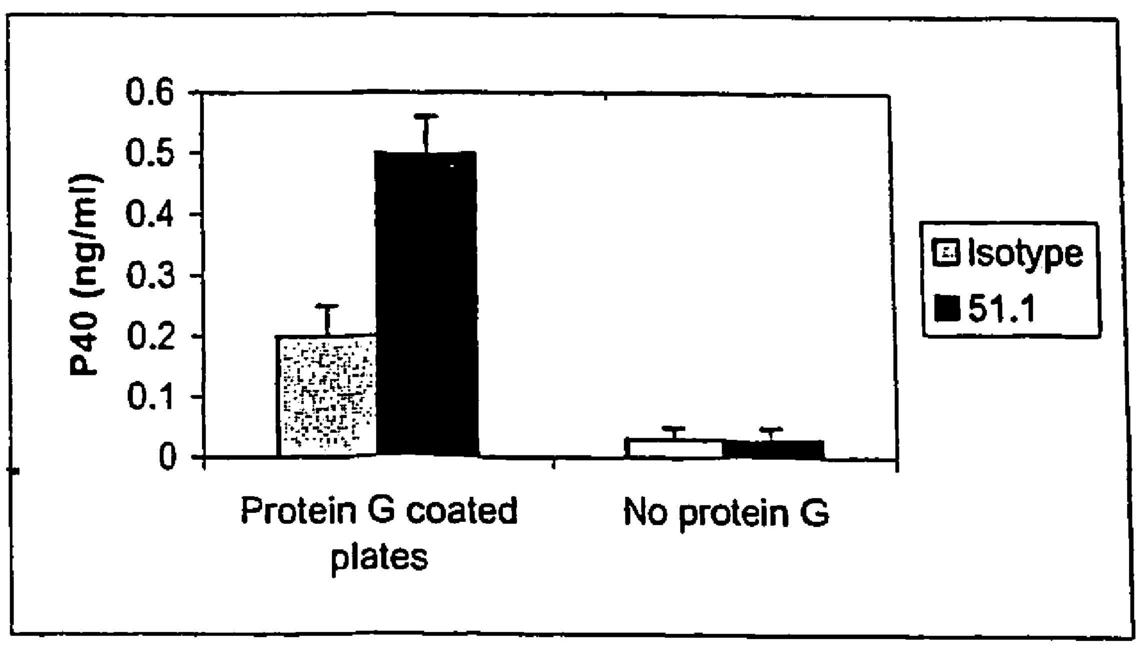
FIG. 29 is a bar graph showing the amount of IL-12 p40 released from THP-1 cells in the presence of IFNγ (20 ng/ml) (n-4). The experiment was stopped after one day of incubation, and the supernatant was collected for IL-12 p40 measurements. The 51.1 anti-CD1 antibody on protein G coated plates was able to cross-link CD1d on THP-1 cells. Cross-linking of CD1d stimulates THP-1 cells to produce IL-12 p40. Cells from control plates that were not coated with protein G prior to 51.1 anti-CD1 antibody binding were unable to stimulate THP-1 cells. The data show that cross-linking of CD1d is important for induction of IL-12 p40 release by the 51.1 anti-CD1 antibody.
Figure 30:
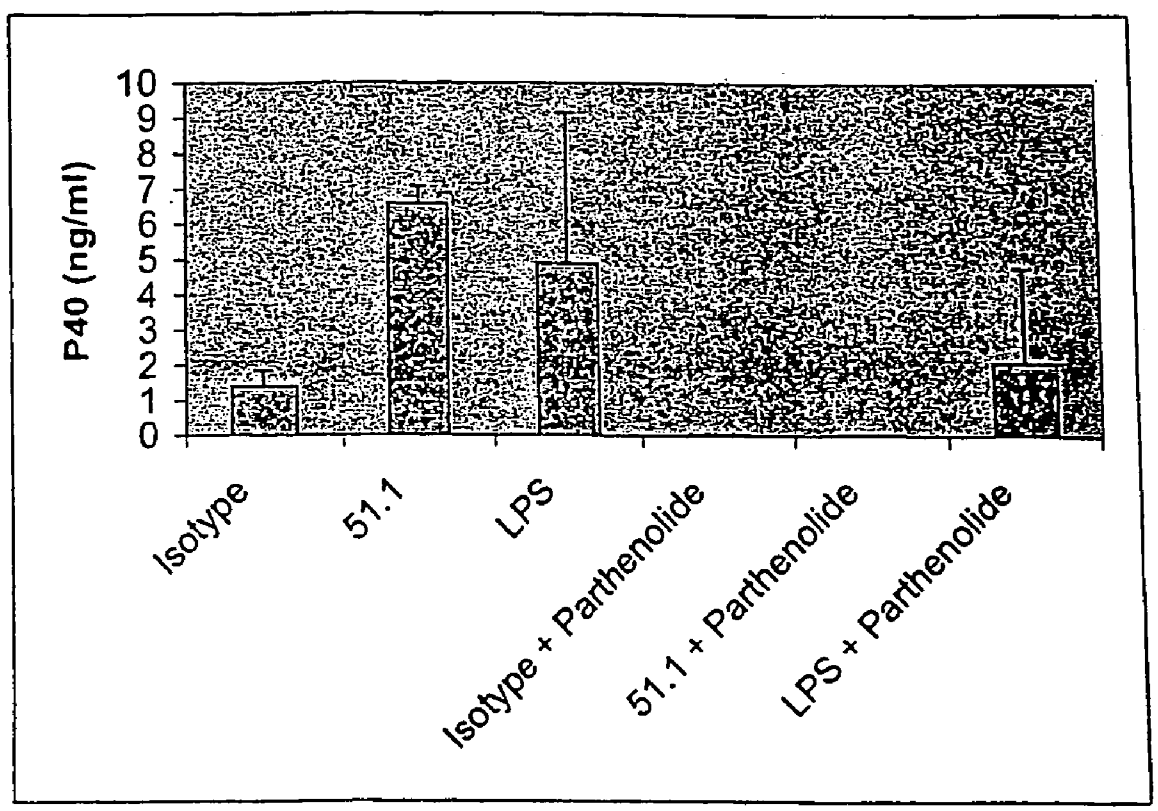
FIG. 30 is a bar graph demonstrating the effect of an NFκB inhibitor (parthenolide, 0.1 μM) on the release of IL-12 p40 by THP-1 cells that is induced by the 51.1 anti-CD1 antibody or LPS (n=4). These data indicate that NFκB is involved in the transcription of IL-12 p40.

The results from the above experiments demonstrate that the 51.1 anti-CD1 antibody induced production of IL-12 (FIGS. 4-11, 14, 15, 21, and 22). FIG. 29 illustrates the results of a similar experiment in which the 51.1 anti-CD1 antibody bound to protein G coated plates induced the release of IL-12 by THP-1 cells in the presence of IFNγ. The NFκB inhibitor parthenolide caused a reduction in the amount of IL-12 p40 that was released by THP-1 cells due to incubation in the presence of the 51.1 anti-CD1 antibody or LPS (FIG. 30), indicating that NFκB is involved in the transcription of IL-12 p40.

The 51.1 anti-CD1 antibody was more potent than CD40 ligation in the stimulation of monocytes to produce bioactive IL-12. Anti-CD1 antibodies can also synergize with antibodies such as anti-CD40 antibodies to stimulate monocytes in vitro. IL-4 and IFNγ also increased the ability of anti-CD1 antibodies to enhance production of IL-12. Even in the absence of anti-CD40 antibodies, anti-CD1 antibodies can activate dendritic cells to produce bioactive IL-12.

The generality of CD1 activation was confirmed using panels of CD1 antibodies. Several monoclonal antibodies to different CD1 epitopes activated the target cells. These results demonstrate that anti-CD1 antibodies are useful in the treatment and prevention of conditions for which increased levels of IL-12 are desirable. Examples of such conditions include cancers and infections by pathogens such as bacteria, viruses, or yeast.

Figure 25:
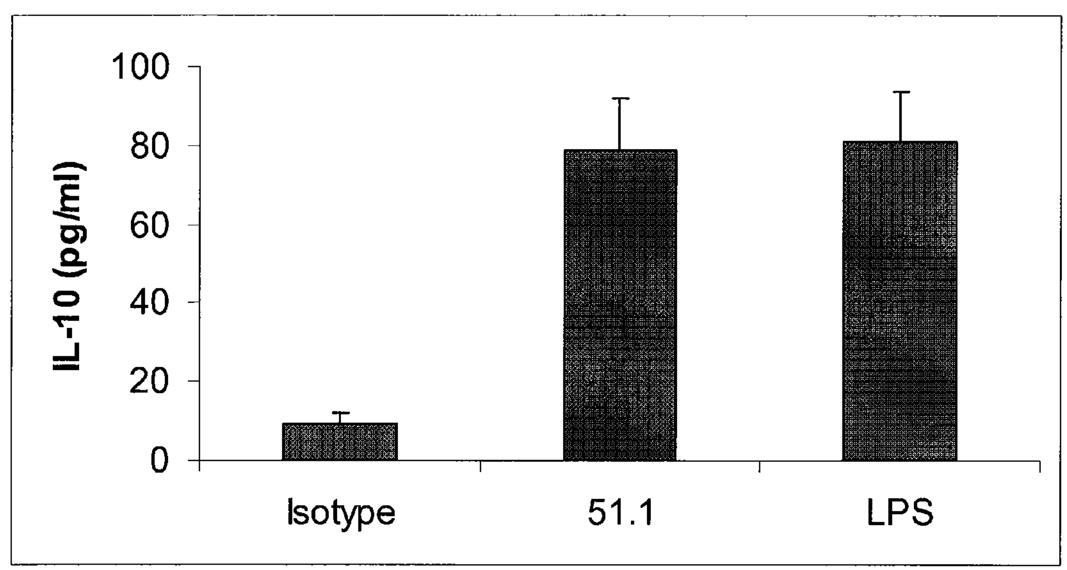
FIG. 25 is a bar graph showing the relatively low amount of IL-1α released from adhered PBMC in the presence of IFNγ (20 ng/ml) (n=4). The experiment was stopped after one day of incubation, and the supernatant was collected for IL-1α measurements. The 51.1 anti-CD1d antibody stimulated the release of IL-1α in an amount similar to that released from LPS-stimulated cells.
Figures 27A, 27B, 27C, 27D:
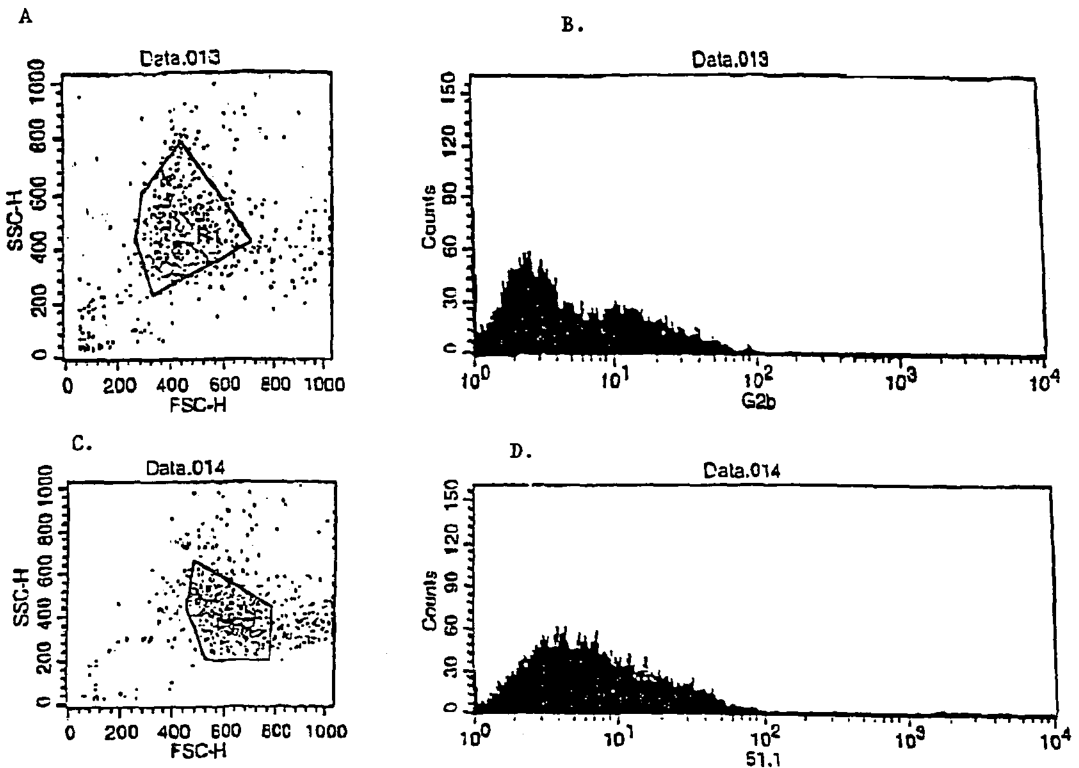
FIGS. 27A-27D are graphs generated from a FACSCAN cytometer showing the absence of external CD1d on the cell surface of C1 Rmocks (negative control).
Figures 28A, 28B, 28C, 28D:
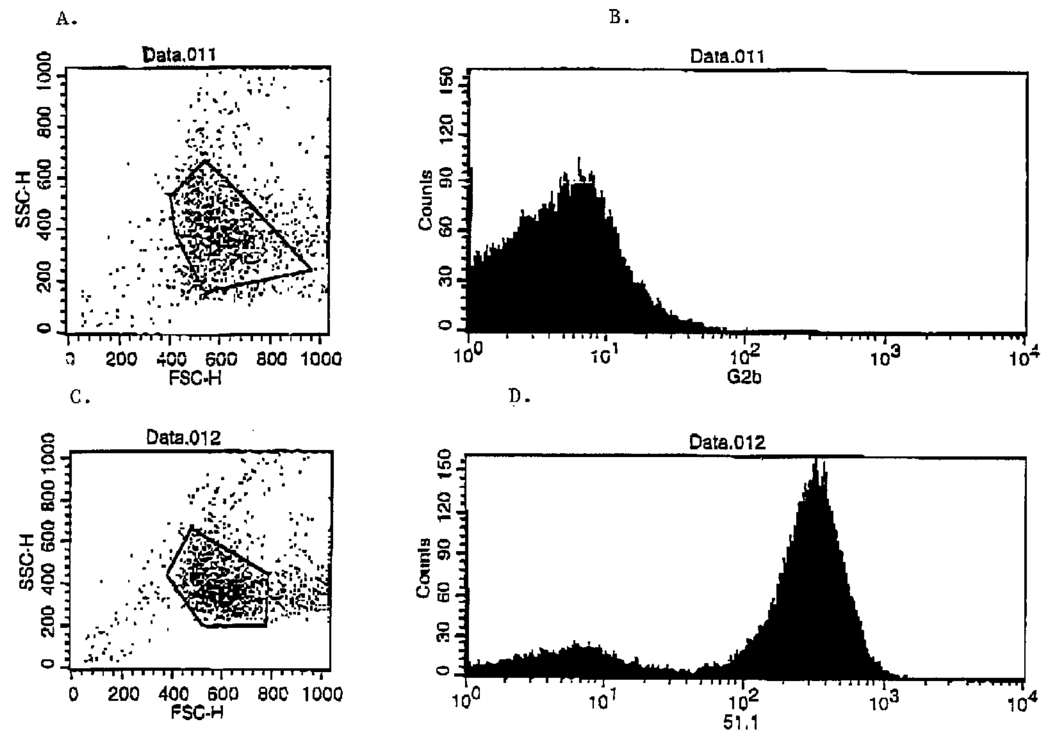
FIGS. 28A-28D are graphs generated from a FACSCAN cytometer showing the presence of external CD1d on the cell surface of C1Rd cells (positive control).
Figure 31:
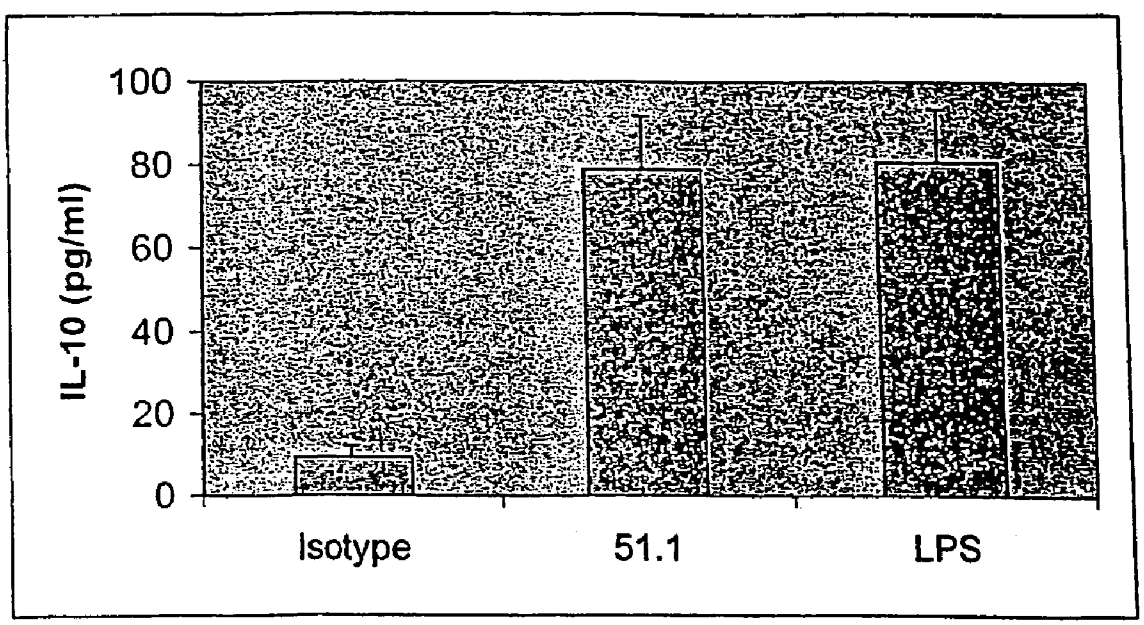
FIG. 31 is a bar graph showing the relatively low amount of IL-10 released from adhered PBMC in the presence of IFNγ (20 ng/ml) (n=4). The experiment was stopped after one day of incubation, and the supernatant was collected for IL-10 measurements. The 51.1 anti-CD1 antibody stimulated the release of IL-10. In particular, the amount of IL-10 released after stimulation with the 51.1 anti-CD1 antibody was similar to the amount of IL-10 released after stimulation with LPS.

In addition to stimulating the release of large amounts of bioactive IL-12, the 51.1 anti-CD1 antibody can also stimulate the release of low levels of IL-10 and IL-1α (FIGS. 25 and 31). IL-10 has a wide range of in vivo biological activities and is a key regulatory cytokine of immune-mediated inflammation. This cytokine has been shown to inhibit the functions of key elements of both innate and acquired immune responses. IL-10 also enhances the function of a recombinant poxvirus-based anti-cancer vaccine and may represent a potential adjuvant in the vaccination against human cancers using recombinant poxvirus-based vaccines. IL-1 has a broad range of physiological effects and is released early in a disease or injury process. For example, IL-1 is an important mediator of inflammation and tissue damage in multiple organs. LPS is a more potent inducer of IL-1, but only stimulates comparable or lower levels of IL-12. Therefore, the ability of the 51.1 anti-CD1 antibody to selectively stimulate the production of IL-12 supports its usefulness for the treatment or prevention of a variety of diseases.

EXAMPLE 4

Administration of Antibodies for In Vivo Activation or Expansion of APCs

One or more anti-CD1 antibodies may be administered to a mammal, possibly in addition to the administration of a cytokine, for the in vivo expansion of APCs for the treatment or prevention of an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer. As described in Example 7, all modes of administration, dosing, and frequency are contemplated. Examples of doses of anti-CD1 antibodies that may be administered to a mammal such as a human include doses that fall within one of the following ranges: 0.1 to 10 mg/kg, 0.1 to 0.4 mg/kg, 0.1 to 1 mg/kg, or 1 to 4 mg/kg, inclusive.

The pharmaceutical compositions containing one or more antibodies of the invention may be prepared as described previously in Remington's Pharmaceutical Sciences by E. W. Martin. Pharmaceutical stabilizing compounds, delivery vehicles, or carrier vehicles may be used. For example, human serum albumin or other human or animal proteins may be used. Phospholipid vesicles or liposomal suspensions are possible pharmaceutically acceptable carriers or delivery vehicles. These compositions can be prepared according to methods known to those skilled in the art.

An antibody of the invention that is covalently linked to a fluorescent label or radiolabel may be used to visualize the in vivo distribution, quantity, or migration of APCs. This imaging of APCs may be used to identify subjects who are at risk for or have an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer. Alternatively, this method may be used to determine the effect of a therapy for one of the above diseases on APCs.

EXAMPLE 5

Optional Cytokine Treatment to Alter the Th1/Th2/Immune Deviation Response Ratio of T Cells While not meant to limit the invention to a particular theory, a working hypothesis is that NK T cells, CD1d-reactive T cells, or J$\alpha$Q$^+$ T cells producing high levels of IL-4 possibly in conjunction with other "Th2" cytokines) will bias toward Th2 immune responses, while high IL-12 (induced from APCs by activated CD1d-reactive T cells) and/or IFN-$\gamma$ (produced by the T cells themselves) relative to IL-4 will drive (or at least be a marker of invariant T cells that will drive) immune responses against tumors or infectious pathogens.

In addition to modulating the immune system by administering an anti-CD1 antibody, NK T cells, CD1d-reactive T cells, or J$\alpha$Q$^+$ T cells may be biased towards Th1-like NK or lymphokine-activated killer (LAK)-like cytotoxicity of invariant T cells, as well as, IFN-$\gamma$ production to potentially augment their in vivo anti-tumor or anti-pathogen activity. For example, IL-12 augments both IFN-$\gamma$ production and, significantly, NK/LAK-like cytotoxicity of invariant T cells have recently been published (van der Vliet et al., Immunology 98:557-63, 1999; WO 01/98357). IL-15, IL-18, and type 1 INFs are also known to enhance Th1 polarization of human T cells. Other cytokines or combinations of cytokines that may bias NK T cells, CD1d-reactive T cells, or J$\alpha$Q$^+$ T cells towards Th1, Th2, or immune deviation responses include IL-2, IL-4, IL-7, IL-8, IL-10, IL-12, IL-13, IL-15, IL-18, IFN-$\alpha$/$\beta$, IFN-$\gamma$, and GM-CSF. The Th2 response may be desirable for the prevention or treatment of an autoimmune disease. Alternatively, for the maintenance of pregnancy, cytokines may be used to bias NK T cells, CD1d-reactive T cells, or J$\alpha$Q$^+$T cells towards immune deviation responses instead of Th1 or Th2 responses.

After administration of one or more of these cytokines, the T cells in a sample from a mammal may be functionally tested for secretion of L-4, IL-10, GM-CSF, and IFN-$\gamma$. The regulation of cytotoxicity against CD1d$^+$(CIR, CD1d), NK' targets (JY, K562, 721.221, and YAC-1), or LAK targets by cytokine supplementation may also be determined (Exley et al., supra (1997); Exley et al., J. Exp. Med. 188:867-876, (1998)).

EXAMPLE 6

Methods for Determining the Effect of Antibodies on the Targeted APC Subpopulation In Vivo Any of the antibodies of the invention may be tested in an in vivo animal or primate model to determine the pharmacological and pharmacokinetic properties of the antibodies. For example, the half-life, bio-distribution, and efficacy of the antibody may be determined.

One possible method involves the administration of human APCs or any other APC population of interest to a SCID or otherwise immune-deficient animal such as a mouse and administration of an anti-CD1 antibody to the animal to determine whether the antibody modulates the activity or number of the administered APCs in vivo.

In particular, a population of APCs that contains 1-10 million APCs of interest is administered i.v. or to any site of interest. One or more antibodies are administered, prior to, concurrent with, or following administration of the APCs. For example, the antibody may be administered at any point during the lifetime of the administered APCs in the host animal. Approximately 1-100 μg of the antibody is administered in the same site or in a different site as the site of administration of the APCs. If detectably labeled antibodies are used, the location and amount of administered antibody and/or APCs may be monitored in vivo based on fluorescence or radioactivity. Additionally, histology, immunological, and/or biochemical measurements may be performed ex vivo on tissues from the animal. The biological activity of the antibody or APC subpopulation may be measured by analyzing the amount or activity of antibodies, growth factors, or cytokines in a serum or tissue sample. Moreover, the activation of other cells, such as T cells, by the administered APC subpopulation may be measured. For example, the number of CD1-reactive T cells may be measured by FACS sorting.

Other animal or primate models of immune or inflammatory disorders and pathogenic infections are known to those skilled in the art and can be readily used to determine the ability of an anti-CD1 antibody or antibody combination or ex vivo expanded APCs (Example 7) to prevent or treat the condition. For example, an animal model of cancer is disclosed by Karnbach et al. (J Immunol 167(5):2569-76, 2001), and an animal model of bacterial infection is disclosed by Lehmann et al. (J Immunol 167(9):5304-15, 2001).

Schwartzman Reaction

One of the classic examples of necrotizing inflammation is the Schwartzman reaction, in which lipopolysaccharide (LPS) is introduced first into rabbit skin and then, 24 hours later, followed by a second intravenous dose of the same LPS (McFadden and Lucas, WO 96/33730; filed Apr. 19, 1996). Within hours after the second LPS injection, infiltrating macrophages induce a reproducible necrotizing response at the site of the primary injection which is highly reproducible and readily quantified. The ability of an anti-CD1 antibody or antibody combination to inhibit this inflammation may be examined.

New Zealand White female rabbits weighing 3 kg are injected with lipopolysaccharide (LPS) of the *E. coli* serotype 0111:B4 (Sigma) and CBP-I (T7) protein which had been purified to homogeneity using column chromatography. Eight intradermal injections (0.1 ml each) of 50-100 μg LPS in the presence and absence of an anti-CD1 antibody is applied to the back of the rabbit; there are 4 injection sites on each side, separated by about 2.5 cm. Twenty-four hours later, 100 μg of LPS is administered to the rabbit intravenously in the marginal ear vein. About 4-6 hours after the intravenous injection, necrotic inflammation typically develops at the sites of intradermal injection of LPS (in the absence of an anti-CD1 antibody). As soon as the inflammation is significant, the rabbit is sacrificed by a lethal injection of euthanol. The size and redness of the lesions are assessed, and tissue samples are collected.

Models of Injury Induced Atherosclerosis

Inflammation has been associated with accelerated atherosclerotic plaque development in the arterial wall. There is a high rate of plaque recurrence, restenosis, after the use of balloon angioplasty and other related angioplasty devices designed to open occluded arteries. Accelerated atherosclerotic plaque growth also has been reported under conditions leading to arterial injury, viral infections, vasculitis, homocystinuria, diabetes melitis, hypertension, hyperlipideuria, smoking, and immune complex generated disorders. Thus, anti-CD1 antibodies can also be tested in the rat and rabbit models of injury induced atherosclerosis disclosed by McFadden and Lucas (WO 96/33730; filed Apr. 19, 1996).

EXAMPLE 7

Expansion and Re-Introduction of Ex Vivo Expanded APCs into Mammals

APCs from a peripheral blood sample (20 ml or from the product of leukopheresis) from a mammal may be enriched prior to ex vivo expansion using FACS sorting or immunoaffinity purification or expanded directly using an anti-CD1 antibody, as described in the previous examples. Additionally, IL-2, IL-7, or a mitogen may be added to stimulate cell expansion. IL-4/GM-CSF may be added to stimulate monocytic cells. If necessary, a secondary ex vivo expansion, possibly after a second enrichment step, may be conducted under conditions used for the primary expansion to increase both cell number and purity. Exemplary amounts of anti-CD1 antibody for stimulation of APCs such as human APCs includes amounts in one of the following ranges: 0.1 to 10 μg, 0.1 to 1 μg, 1 to 5 μg, or 5 to 10 μg per one ml of cells with a concentration of 0.5 to $1\times10^6$ cells per ml. After stimulation, the cells may be assayed for purity and for production of an antibody, cytokine, or growth factor as described above. Desirably at least $10^6$, more desirably at least $10^8$, and most desirably at least $10^9$ APCs are obtained after expansion. Desirably, the APCs are at least 60%, 80, or 90% pure, based on the presence of CD1 and/or other APC markers, and maintain the production of cytokines, antibodies, and/or growth factors.

If secondary stimulations do not yield adequate cell numbers, then additional rounds of stimulation may be used. Alternatively, the number of starting cells may be increased by using larger blood samples or through leukopheresis. In this case, an initial enrichment of APC may be performed by positive selection using the 27.1, 42.1, 51.1 or similar monoclonal antibodies conjugated to beads. To increase purity, the APCs may also be purified by FACS or antibody conjugated to beads prior to re-infusion. Additionally, the therapeutic potential of cellular reinfusion of expanded polyclonal APC lines may be compared to that of expanded APC clones, or pools thereof.

It is not intended that the administration of ex vivo expanded APCs be limited to a particular mode of administration, dosage, or frequency of dosing; the present mode contemplates all modes of administration, including intramuscular, intravenous, intraarticular, intralesional, subcutaneous, or any other route sufficient to provide a dose adequate to prevent or treat an autoimmune disease, viral infection, bacterial infection, parasitic infection, infection by a eukaryotic pathogen, allergy, asthma, inflammatory condition, host versus graft disease, spontaneous abortion, pregnancy, or cancer. Desirably, the cells are re-introduced into the mammal from which the blood sample was taken. It is also contemplated that the cells may be administered to a different mammal. The cells may be administered to the mammal in a single dose or multiple doses. When multiple doses are administered, the doses may be separated from one another by, for example, one week to one month. Examples of doses of ex vivo expanded APCs include between $10^4$ and $10^{10}$ cells, such as between $10^6$ cells and $10^9$ cells. As mentioned in Example 5, one or more cytokines may also be administered before, during, or after administration of the cells. It is to be understood that for any particular subject, specific dosage regimes should be adjusted over time according to the individual need and the professional judgement of the person administering or supervising the administration of the compositions. Additionally, the APCs may be re-introduced as resting or activated cells, depending on the application. Resting cells would require in vivo activation.

OTHER EMBODIMENTS

From the foregoing description, it will be apparent that variations and modifications may be made to the invention described herein to adopt it to various usages and conditions.

All publications, patents, and patent applications mentioned in this specification are herein incorporated by reference to the same extent as if each individual publication, patent, and patent application was specifically and individually indicated to be incorporated by reference.

What is claimed is:

1. A method of treating a mammal having cancer, said method comprising administering to said mammal an anti-CD1d antibody or antibody fragment having the ability to bind CD1d in an amount sufficient to treat said cancer, wherein said antibody or antibody fragment is capable of activating antigen presenting cells that express CD1d.

2. The method of claim 1, wherein said mammal is a non-rodent mammal.

3. The method of claim 2 or 1, wherein said administration is intramuscular, intravenous, intraarticular, intralesional, subcutaneous, or intraperitoneal.

4. The method of claim 2 or 1, wherein said antibody is administered with a pharmaceutically suitable carrier.

5. The method of claim 2 or 1, wherein said mammal is a human.

6. The method of claim 2 or 1, further comprising administering IL-12 to said mammal.

* * * * *

UNITED STATES PATENT AND TRADEMARK OFFICE

CERTIFICATE OF CORRECTION

PATENT NO. : 8,084,020 B2
APPLICATION NO. : 10/513109
DATED : December 27, 2011
INVENTOR(S) : Exley et al.

It is certified that error appears in the above-identified patent and that said Letters Patent is hereby corrected as shown below:

Title Page 2, Item (56) under OTHER PUBLICATIONS, Col. 2, Line 34, in Lehman et al. replace "*Salmonella enteritidis*" with --*Salmonella* Enteritidis--.

In the Specifications:

Column 7, Line 12, replace "*acanthainoebae*" with --*acanthamoebae*--;

Line 21, replace "*K oxytoca*" with --*K. oxytoca*--;

Line 25, replace "*Y pestis*" with --*Y. pestis*--;

Line 31 - 32, replace "*V parahaemolyticus*" with --*V. parahaemolyticus*--;

Line 34, replace "*K kingae*" with --*K. kingae*--;

Line 34 - 35, replace "*M atlantae*" with --*M. atlantae*--;

Line 35, replace "*M lacunata*" with --*M. lacunata*--;

Line 35, replace "*M osloensis*" with --*M. osloensis*--;

Line 40 - 41, replace "*M leprae*" with --*M. leprae*--;

Line 41, replace "*C ulcerans*" with --*C. ulcerans*--;

Line 43, replace "*C coyleae*" with --*C. coyleae*--;

Line 44, replace "*C. itnitans*" with --*C. imitans*--;

Line 46, replace "*C riegelii*" with --*C. riegelii*--;

Line 48, replace "*C urealyticum*" with --*C. urealyticum*--;

Line 53, replace "*S. epiderinidis*" with --*S. epidermidis*--;

Line 54, replace "*S. internedius*" with --*S. intermedius*--.

Signed and Sealed this
Twenty-third Day of April, 2013

Teresa Stanek Rea
*Acting Director of the United States Patent and Trademark Office*